United States Patent [19]

Gilboa

[11] Patent Number: 5,658,775

[45] Date of Patent: Aug. 19, 1997

[54] DOUBLE COPY RETROVIRAL VECTOR

[75] Inventor: Eli Gilboa, Scarsdale, N.Y.

[73] Assignee: Sloan-Kettering Institute for Cancer Research, New York, N.Y.

[21] Appl. No.: 380,935

[22] Filed: Jan. 31, 1995

Related U.S. Application Data

[63] Continuation of Ser. No. 934,310, Aug. 24, 1992, abandoned, which is a continuation of Ser. No. 353,391, May 17, 1989, abandoned, which is a continuation-in-part of Ser. No. 196,628, May 17, 1988, abandoned.

[51] Int. Cl.$^6$ .............................. C12N 15/86; C12N 5/10
[52] U.S. Cl. ................... 435/172.3; 435/69.1; 435/320.1
[58] Field of Search .......................... 435/320.1, 172.3, 435/69.1, 240.1, 240.2

[56] References Cited

U.S. PATENT DOCUMENTS 5,324,643  6/1994  Greatbatch et al. ................ 435/91.32

OTHER PUBLICATIONS

M.A. Lopata et al (1986) Proc Nat. Acad. Sci USA 83:6677–6681.

L.I. Lobel et al (1985) Science 228:329–332.

W. Reik et al (1985) Proc. Natl. Acad. Sci. USA 82: 1141–1145.

L.I. Lobel et al (1984) Proc. Natl. Acad. Sci. USA 81: 4149–4153.

H. Temin (1986) In: Gene Transfer, (Ed: R. Kucherlapati) Plenum Press, NY, 149–187.

J. P. Dougherty et al (1987) Proc. Natl. Acad. Sci. USA 84: 1197–1201.

*Primary Examiner*—Mindy Fleisher
*Assistant Examiner*—Johnny F. Railey, II
*Attorney, Agent, or Firm*—John P. White

[57] ABSTRACT

The present invention concerns a retroviral vector for introducing into a eucaryotic cell DNA encoding a transcription unit which comprises a first DNA sequence which is the reverse transcript of at least a portion of a retrovirus, said portion including both the 5' LTR sequence and the 3' LTR sequence of the retrovirus, and a second DNA sequence encoding the transcription unit which is inserted into the U3 region of the 3' LTR sequence. A method of producing a virion useful for introducing into a eucaryotic cell DNA encoding a transcription unit is provided as well as a method of introducing into a eucaryotic cell DNA encoding a transcription unit which comprises infecting the cell with such a virion.

34 Claims, 19 Drawing Sheets

FIGURE 3
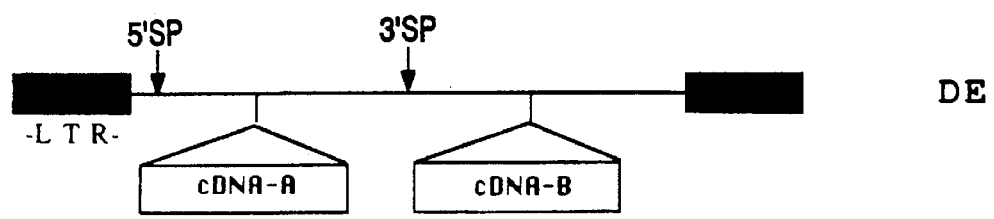
DE
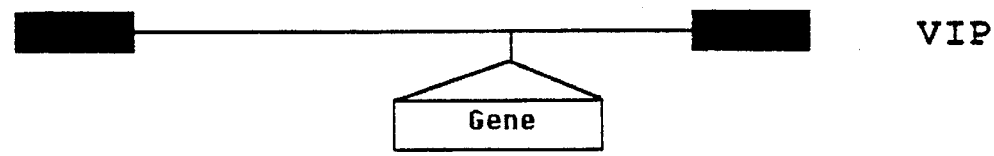
VIP
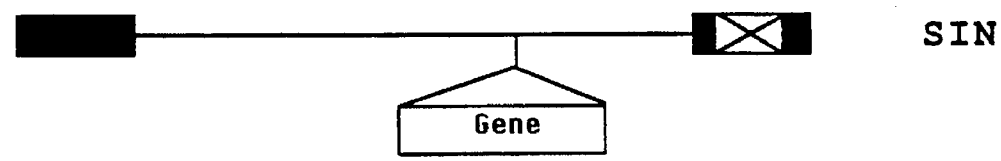
SIN
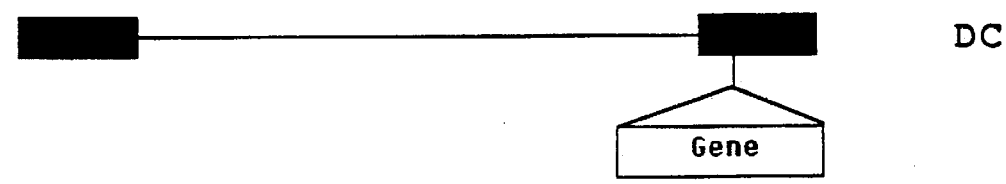
DC

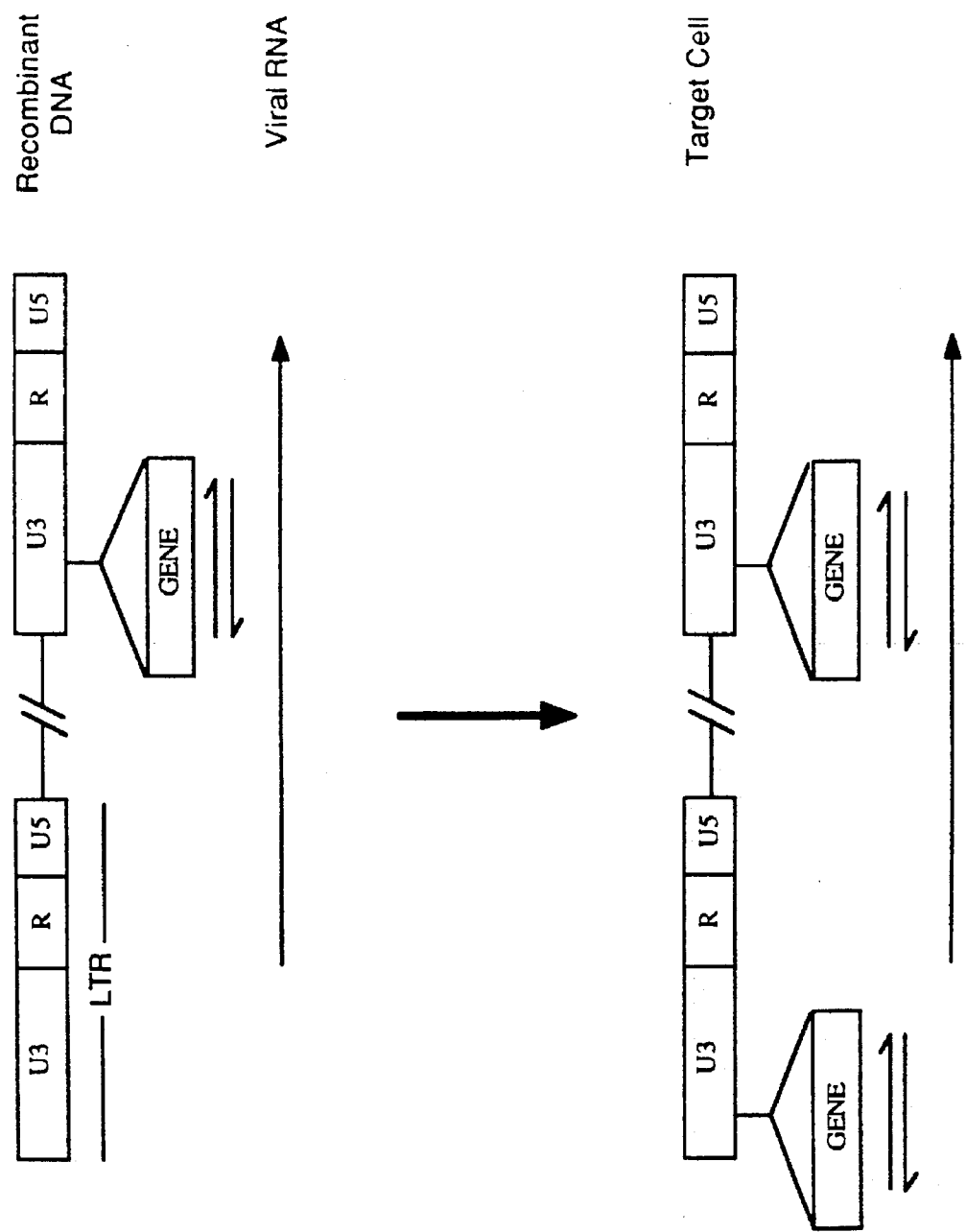

FIGURE 7A
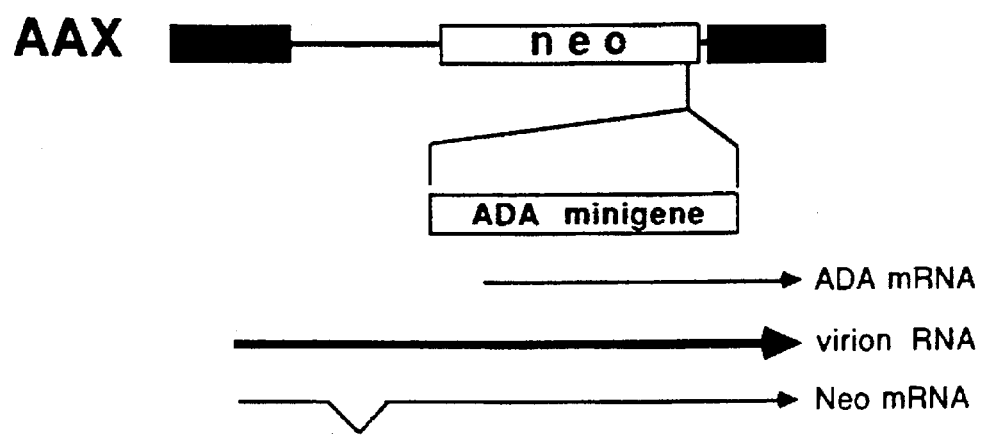
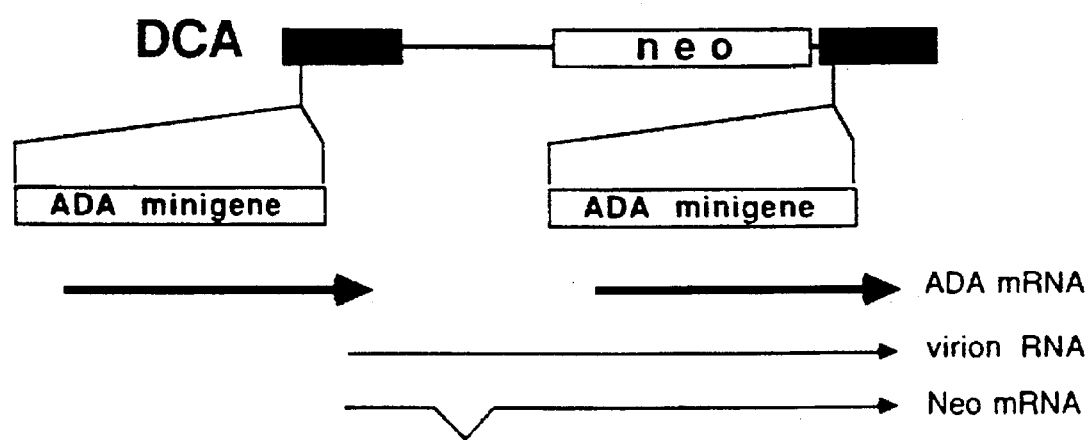

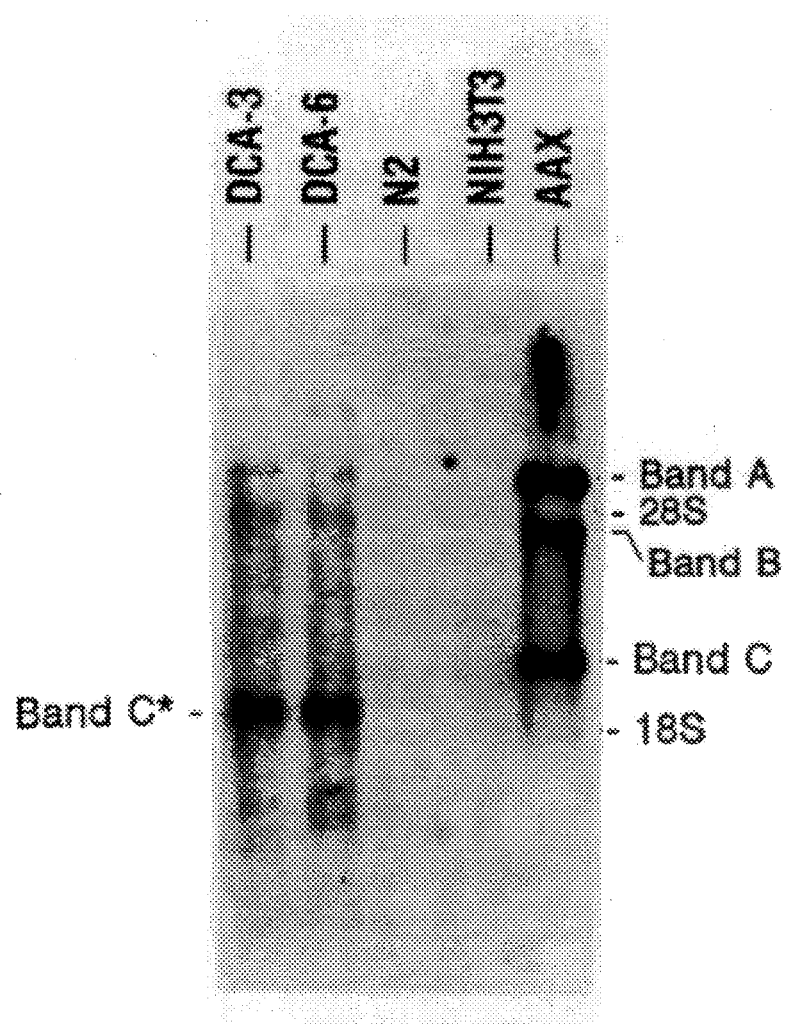

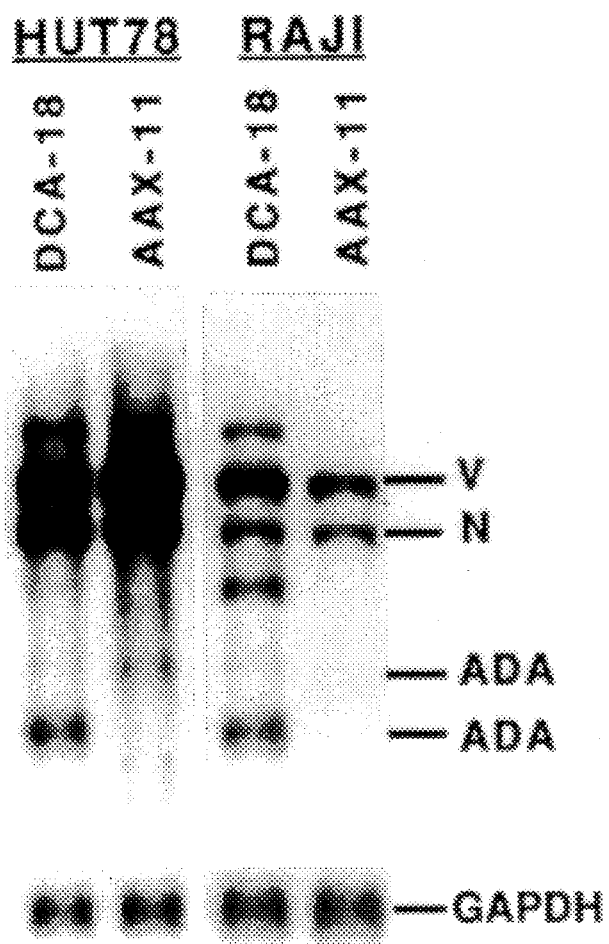

DOUBLE COPY RETROVIRAL VECTOR

This is a continuation of application Ser. No. 07/934,310, filed Aug. 24, 1992, now abandoned, which is a continuation of application Ser. No. 07/353,391, filed May 17, 1989, now abandoned. This application Ser. No. 07/353,391 is a continuation-in-part application of U.S. Ser. No. 07/196,628, filed May 17, 1988, which is now abandoned.

This invention was made with support from the U.S. Government under grant number CA-33050-06, from the National Cancer Institute, U.S. Department of Health and Human Services. The U.S. Government has certain rights in this invention.

Throughout this application various publications are referenced and citations are provided for them. The disclosures of these publications in their entireties are hereby incorporated by reference into this application in order to more fully describe the state of the art to which this invention pertains.

BACKGROUND OF THE INVENTION

The understanding of gene expression has been greatly enhanced by the ability to transfer cloned genes into cells and to study the mechanism of their regulation. For the past several years it has been recognized that retroviruses are good candidates as vehicles or vectors to introduce genes into eucaryotic cells. Retro-virus-derived vectors utilize the biochemical processes unique to this group of viruses to transfer genes with high efficiency into a wide variety of cell types in vitro and in vivo. By using retrovirus-derived vectors, the effect of newly introduced genes and the mechanism of gene expression can be studied in cell types, so far refractory, to other methods of gene transfer. The special features of this new gene transfer technology have provided for the first time the opportunity of introducing genes into the somatic cells of live animals. Although at present, gene transfer technology is mainly limited to gene transfer into hemopoietic cells, its potential in general studies and applications to human therapy is beginning to be recognized.

As with many new emerging technologies, the potential of retroviral gene transfer created great expectations. It was quickly realized that retroviral gene transfer is not a simple technique to adapt, and the initial euphoria gave vent to overt pessimism. Recent progress in this field is encouraging, and there is perhaps reason for cautious optimism that some of the expectation generated by this new gene transfer technique will be fulfilled.

PRINCIPLES OF RETROVIRAL GENE TRANSFER

Retroviruses are RNA viruses wherein the viral genes are encoded in a single-stranded RNA molecule. After penetration into the cell, the vital RNA is converted into a double-stranded DNA molecule in a process called reverse transcription. The DNA enters the nucleus and integrates into the cell chromosome, becoming indistinguishable from any other cellular gene. The integrated viral DNA form, which is called a provirus, is the template for the expression of the viral genes and the synthesis of the progeny virion RNA. The viral gene products and progeny RNA assemble into a virion which leaves the cell by budding through the outer membrane.

It is important to point out that the integration of the viral genome into the cell chromosome is an obligatory part of the viral replication process and is mediated by virally encoded enzymes. With a few exceptions, the presence of the vital genome in the cell, expression of its genes, and the formation of progeny virus have no apparent effect on the viability of the infected cell. The cell is chronically infected but otherwise healthy, and continuously secretes virus into medium (see Varmus and Swanstrom, 1985 (19) for a review).

Retroviral gene transfer is used for the purpose of introducing functional genes into cells at one copy per cell, without affecting the proliferative capacity of the recipient cell. The suitability of retroviruses for gene transfer stems from their mode of replication. By "simply" replacing the vital genes with the gene of interest and utilizing the efficient vital infection process, the gene is transferred into the target cell as if it were a viral gene. FIG. 1 is a schematic diagram showing how this process works. First, using standard recombinant DNA techniques, portions of the vital DNA are combined with the gens of interest. As shown in FIG. 1, most of the internal vital sequences may be replaced with the foreign gene. The remaining retroviral DNA is called the vector and always includes the two ends of the viral genome, which are terminally redundant and are called long terminal repeats (LTRs). This and immediately adjacent regions of the vital genome contain important cis functions necessary for the replication of the virus, for example, the viral packaging signal as shown in FIG. 1. The deleted sequences, which may be replaced with the foreign gens or genes, encode viral proteins that are necessary for the formation of infectious virions. These proteins, although necessary for the replication of the virus, can be complemented in trans if the cell contains another virus expressing the gone products missing in the vector. In the second step, the hybrid DNA is introduced into specially engineered cells by standard (and inefficient) DNA transfection procedures. These cells, called packaging cells, harbor a retrovirus defective in a cis function. The RNA of such cells cannot encapsidate into a virion but it does express all the vital proteins and is therefore able to complement the same functions missing in the incoming vector DNA. The vector DNA is now transcribed into a corresponding RNA which is encapsulated into a retrovirus virion and is secreted into the medium. The actual gene transfer takes place at this point: the virus collected in the medium is used to infect the target cells, and through the efficient vital infection process the foreign gene is inserted into the cell chromosome as if it were a vital gene. (For additional reading see Coffin, 1985 (4); Temin, 1986 (18); and Gilboa, 1986 (7)).

Retroviral based gens transfer is a promising technique for two principal reasons. The first reason is high efficiency. At present retroviral based gene transfer is the only system available for use in cases where it is necessary to introduce the gene of interest into a large proportion of the target cells. This is in sharp contrast to other gene transfer systems such as DNA transfection, protoplast fusion and electroporation. Second, retroviral vectors have a broad host range, which enables genes to be introduced not only into monolayer-grown cells such as NIH 3T3 or L cells but also into many suspension-grown lymphoid and myeloid cells and the hemopoietic stem cells present in the bone marrow population (see Gilboa, 1986 (7) for a review).

The basic limitation of using retroviral vectors compared to alternative types of gene transfer techniques is that it requires extra manipulations, and is thus more time-consuming. When using DNA transfection, electroporation or protoplast fusion, the DNA fragment carrying the gene of interest is directly introduced into the target cells, whereas in using retroviral vectors the gens of interest is first inserted into a retroviral vector and converted into a virion before the actual gene transfer takes place (FIG. 1). With numerous refinements it is now quite simple to insert a gens into a retroviral vector, obtain recombinant virus, infect target cells and express the foreign gene. What is, however, more difficult and elusive at the present time is how to maximize the efficiency of the process. Three parameters determine the efficiency of retroviral gene transfer. The first parameter is the stability of the recombinant virus carrying the gene of interest, reflecting the observation that some inserts are unstable within the context of a retroviral vector. The second parameter is the ability to infect a large proportion of target cells. This property is a function of the titer of recombinant virus that can be produced in the process, as described in FIG. 1. The titer of retroviral vectors is an important and limiting parameter of this technology. The third and critical parameter of this technology is the ability to express the transduced gene in the infected cells. This is probably the most problematic aspect of this technology.

RETROVIRAL VECTOR DESIGN

The nature of the retrovirus vector will determine such parameters to a large extent. The reason why the development of an all-purpose, super-efficient, retroviral vector is elusive, stems from a lack of understanding of some of the more subtle details of the structure and biology of retroviruses, as well as that of mammalian genes. Difficulties often arise when the hybrid virus is constructed by replacing viral genes with a foreign gene (FIG. 1). The removal of viral sequences and substitution with foreign DNA can cause a substantial reduction in the titer of viruses generated and can also reduce the efficiency with which the transduced gene is expressed. A more significant limitation associated with the use of retroviral vectors is the inability to express the transduced gene. This limitation is inherent in the design of most retroviral vectors and the new vector system described in the present invention is designed primarily to circumvent or alleviate this problem.

Several strategies of retroviral vector design are shown in FIG. 2, to highlight the advantages and limitations of each approach. Note that these vectors accommodate not one but two genes. One gene is the gene of interest and the second gene is a selectable gene. A selectable gene is not absolutely required, but its presence greatly facilitates the use of retroviral vectors, enabling the identification and isolation of productively infected cells. In some cases, the presence of a selectable gene may have negative effects, and the use of vectors without selectable genes, although more cumbersome, may be advantageous. FIG. 2A shows the structure of a prototype double expression (DE) vector as described by Cepko et al., 1984 (3). As shown in FIG. 2A (top), the three viral genes are expressed from two RNA species. The gag and pol genes are expressed from an unspliced RNA from which is co-linear with the viral genome and the env gene is expressed from a spliced RNA form, generated from the unspliced RNA species by the removal of a long intron. Removal of the viral intron is tightly regulated in this system, because both RNA species, the spliced form and its precursor, the unspliced form, accumulate in the cytoplasm. DE vectors (FIG. 2A, bottom) contain two foreign genes. One gene, replacing the gag/pol segment, is expressed from the unspliced RNA form and the second gene, replacing the viral env gene, is expressed from the spliced RNA form. The distinguishing feature of this type of vector is that it provides not only the cis functions necessary for the transmission of the foreign genes into the target cells but also provides the cis functions for their expression, i.e., an enhancer, a promoter and the 5' splice site in the 5' LTR and downstream sequences, a poly A signal in the 3'LTR, and a 3' splice site encoded in a third DNA fragment. DE vectors are dependent on the efficient formation of the viral RNA species. This in turn depends on a properly regulated splicing process, and the underlying assumption in the design of these vectors was that removal of the viral intron is regulated by the sequences immediately surrounding the splice junctions. There is now mounting evidence indicating that this assumption is not valid. Rather, sequences scattered throughout the viral intron have been found to play an essential role in modulating the levels of spliced and unspliced RNA forms that accumulate in the cytoplasm (9,15). Thus, the absence of intron-contained sequences in DE vectors may be one reason for their poor performance. A second and more important limitation in using DE vectors is inherent in their structure. In DE vectors the expression of the gene of interest is directed from the promoter encoded in the LTR and, therefore, the usefulness of these vectors will be limited to cells in which the viral promoter is sufficiently active.

FIG. 2B shows the structure of another type of retroviral vector in which the transduced gene is expressed from an internal promoter, hence the name, vectors with internal promoters (VIP). In these vectors, the selectable gene is linked to the left end of the viral DNA and is expressed from the viral promoter. A complete gene, or a minigene as shown in FIG. 2B, is inserted downstream of the selectable gene (14). The promoter-encoding DNA fragment, which is responsible for the expression of the transduced gene can be derived from any gene and, therefore, in using this type of vector one has the flexibility of choosing the promoters to express the transduced gene in a manner most appropriate for a particular experimental design.

The main drawback of this strategy of vector design is that an internal promoter is placed within the retroviral transcriptional unit which in turn affects the activity of the internal promoter, and results in variable and often low levels of expression of the transduced gene. This is expected since it has been shown repeatedly that the activity of promoters is reduced when present downstream to another active promoter (5,10). Interference of promoter activity occurs also when the two transcriptional units are facing each other (18). FIG. 2B (bottom) shows the structure of a VIP vector called N2 (1). The unique feature of this vector is the generation of significantly higher titers of virus, as compared to other retroviral based vectors. As shown in FIG. 2B (bottom), in the N2 vector the region downstream from the 5' LTR extends beyond the gag AUG initiation codon and includes 418 base pairs of the gag coding sequences to which the bacterial Neo gene is fused. It appears that this extra region present in N2 is responsible for the production of 10- to 50-fold higher titers of virus as compared to similar vectors lacking these sequences (1, 2). For this reason, N2 based vectors are gaining increasing popularity in many laboratories, in particular for the introduction of genes into cultured hemopoietic cell lines and fresh bone marrow cells.

Although N2 based vectors generate high titers of virus, expression of transduced genes is often disappointingly low due to the presence of an active retroviral transcriptional unit. To address this problem another type of retroviral vector called the SIN vector has been developed (23) and similar vectors based on the same principle were later introduced by other laboratories (6,8,22). Self inactivating (SIN) vectors are shown in FIG. 2C and have a very interesting property. The LTRs at the two ends of the retroviral genome encode the enhancer and promoter elements which are responsible for the formation of the viral transcriptional unit leading to the inhibition of gene expression of VIP vectors as described above. The retroviral enhancer can also activate adjacent oncogenes when integrated into the cell chromosome. This is of course a worrisome aspect if retroviral vectors are to be used in human therapy. As its full name implies, the special property of the SIN vector stems from the fact that upon integration into the chromosome of the target cells it self-inactivates, because a small portion of the viral DNA which includes the enhancer and promoter sequences is absent from both LTRs. Consequently, the proviral DNA in the infected cells becomes transcriptionally inactive, enabling the uninhibited expression of the foreign gene. In addition, the absence of the viral enhancers will diminish the possibility of activating cellular oncogenes. FIG. 2C illustrates how this works. SIN vectors contain a small deletion in the 3' LTR which encompasses the promoter and enhancer sequences that control the accurate and efficient transcription of the vital genome. These sequences are required for vital gene expression when present in the 5' LTR but not when present in the 3' LTR and, therefore, their removal from DNA constructs as shown in FIG. 2C, does not affect viral functions. Because a region of the 3' LTR encompassing this deletion, called the U3 region, is the template for the synthesis of the U3 regions in both the 5' and 3' LTRs in the next generation, the deletion encompassing the viral enhancer and promoter will be transferred to both LTRs in the target cells (23).

Although it has been demonstrated that SIN vectors do self inactivate in the target cell, the titers of virus generated from this type of vector are disappointingly low ($10^3$–$10^4$ cfu/ml) and are probably not sufficient for use in applications involving in vivo gene transfer. A systematic effort over a two year period aimed at improving the titer of SIN vectors was not successful (Yu and Gilboa, unpublished result).

In summary, the usefulness of double expression vectors (DE vectors, FIG. 2A bottom) is limited primarily because expression of the transduced gene is restricted to the viral LTR. The use of vectors with internal promoters (VIP vectors, FIG. 2B) circumvents this limitation and the N2 variant shown in FIG. 2B also generates a high titer of virus, a critical parameter of this technology. However, a serious drawback of this type of vector design is the unpredictable and often low level of expression of the transduced gene due to the presence of an active readthrough retroviral transcriptional unit. The development of self-inactivating vectors (SIN vectors, FIG. 2C) was designed to address this problem. Unfortunately, this type of vector, unlike N2 based vectors, yield low titers of virus which severely limits their usefulness, especially for gene transfer into human bone marrow cells. Clearly, although considerable progress has been made in the development of retroviral vectors, the need for more efficient vectors exists, which will yield high titers of virus and also allow for the efficient and uninhibited expression of the transduced gene.

This section on vector design follows in part the outline of a similar section presented in Gilboa, 1986 (7). (For additional details on this subject please consult also Coffin, 1985 (4) and Temin, 1986 (18)).

SUMMARY OF THE INVENTION

The present invention concerns a retroviral vector for introducing into a eucaryotic cell DNA encoding a transcription unit which comprises a first DNA sequence which is the reverse transcript of at least a portion of a retrovirus, said portion including both the 5' LTR sequence and the 3' LTR sequence of the retrovirus, and a second DNA sequence encoding the transcription unit which is inserted into the U3 region of the 3' LTR sequence.

This invention also provides a method of producing a virion useful for introducing into a eucaryotic cell DNA encoding a DNA transcription unit comprising transfecting a eucaryotic cell with the retroviral vector described above into a suitable packaging cell line under conditions such that the virion is formed within, and excreted by, the packaging cell line.

This invention further provides a method of introducing into a eucaryotic cell DNA sequence encoding a transcription unit of interest which comprises infecting the cell with the virion described above, under conditions such that the DNA sequence encoding the transcription unit of interest is incorporated into the chromosomal DNA of the eucaryotic cell.

BRIEF DESCRIPTION OF THE FIGURES

FIG. 3. The basic structural difference between a DC vector and previously designed vectors.

FIG. 4. The principle of double copy (DC) vectors.

Figure 1:
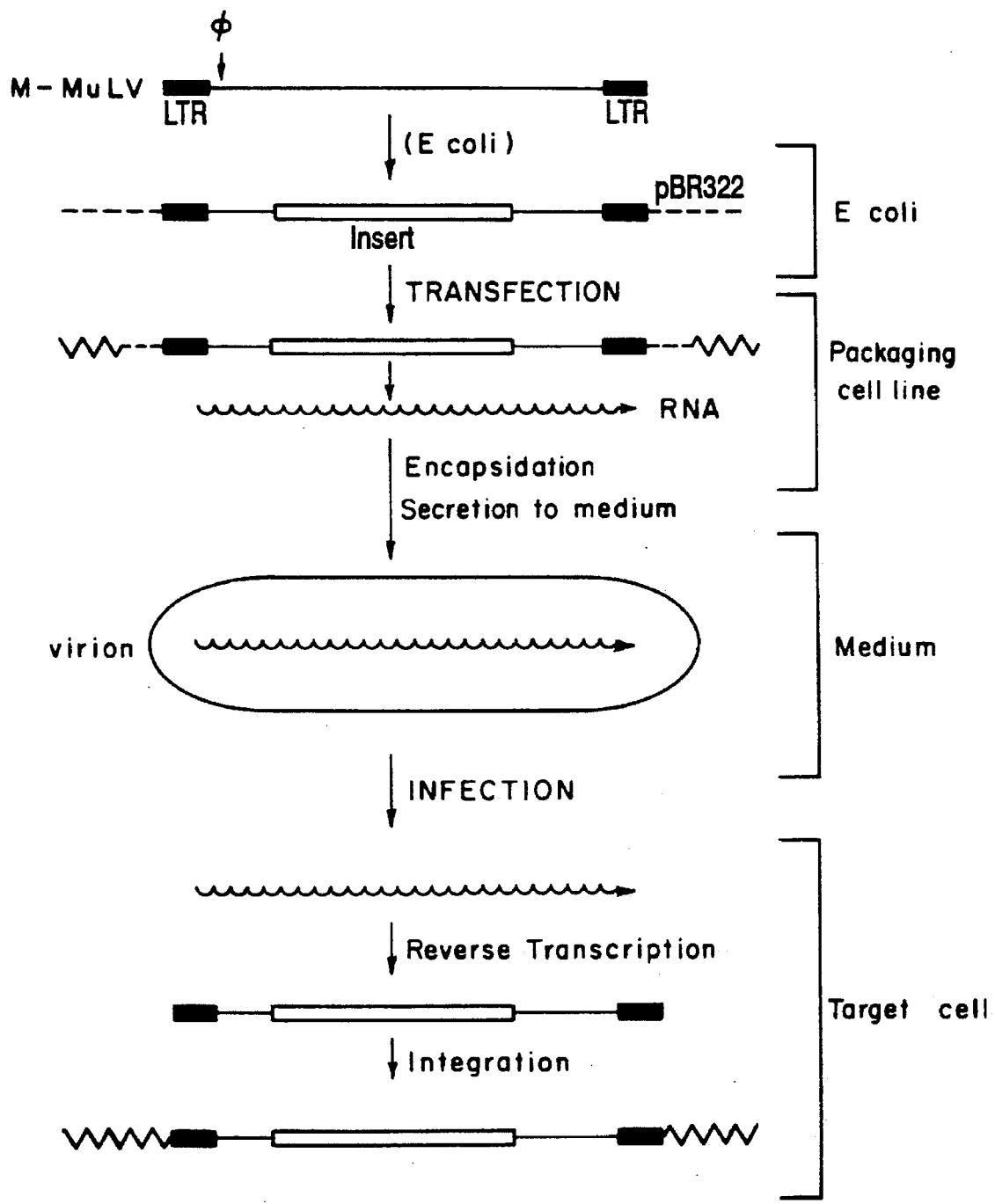
FIG. 1. Use of retroviral vectors to introduce genes into eucaryotic cells. See text for details.
Figure 2A:
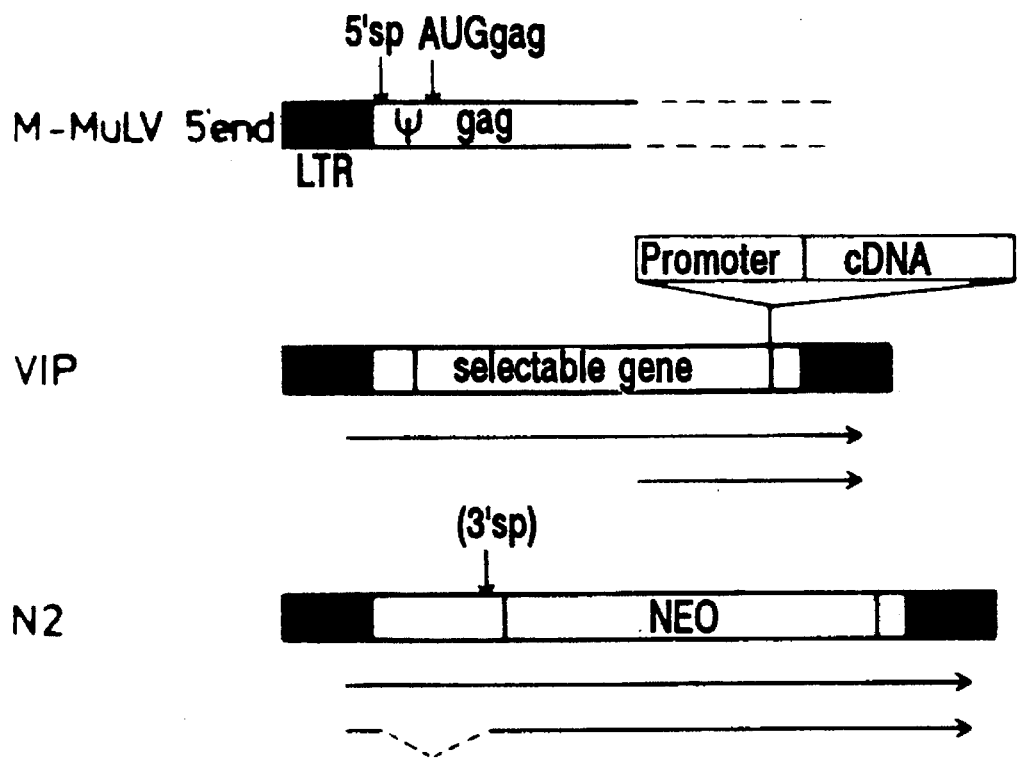
FIG. 2 parts A–C. Strategies of retroviral vector design. See text for details.
Figure 2B:
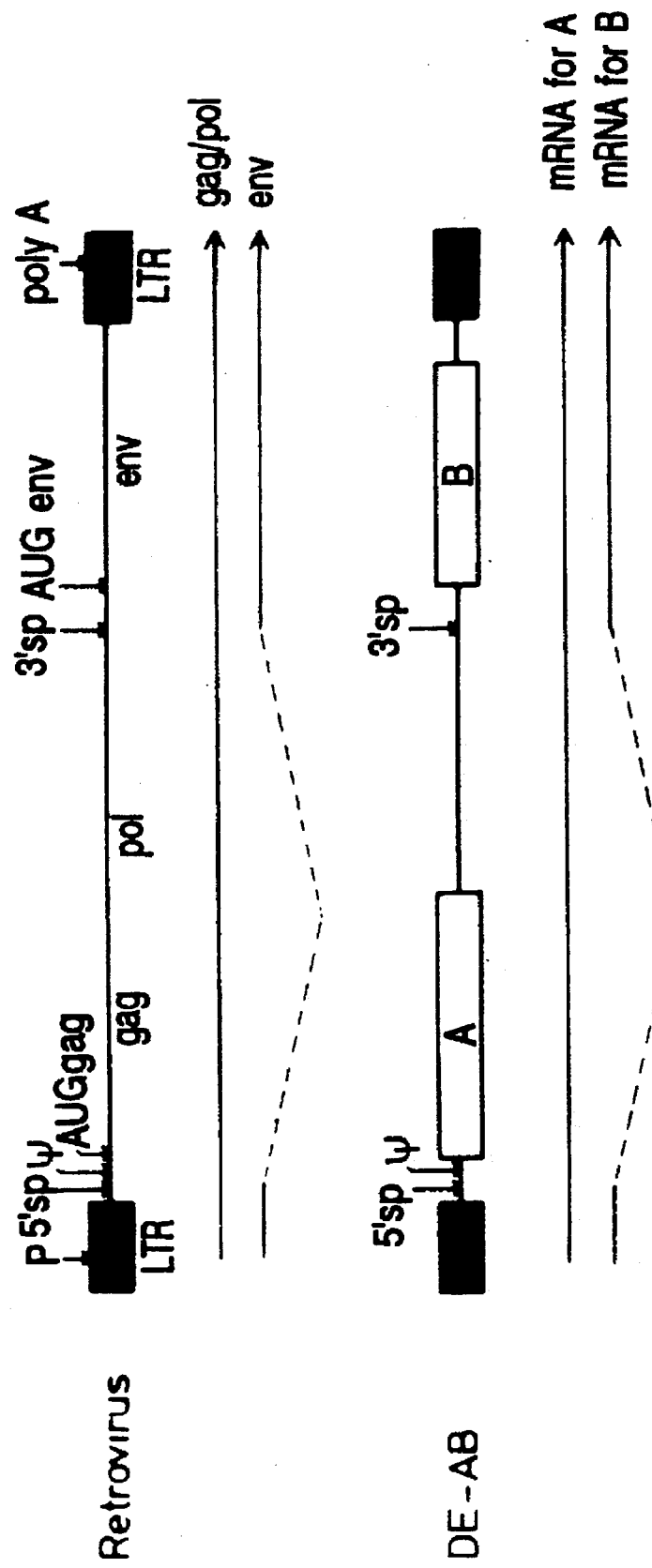
Figure 2C:
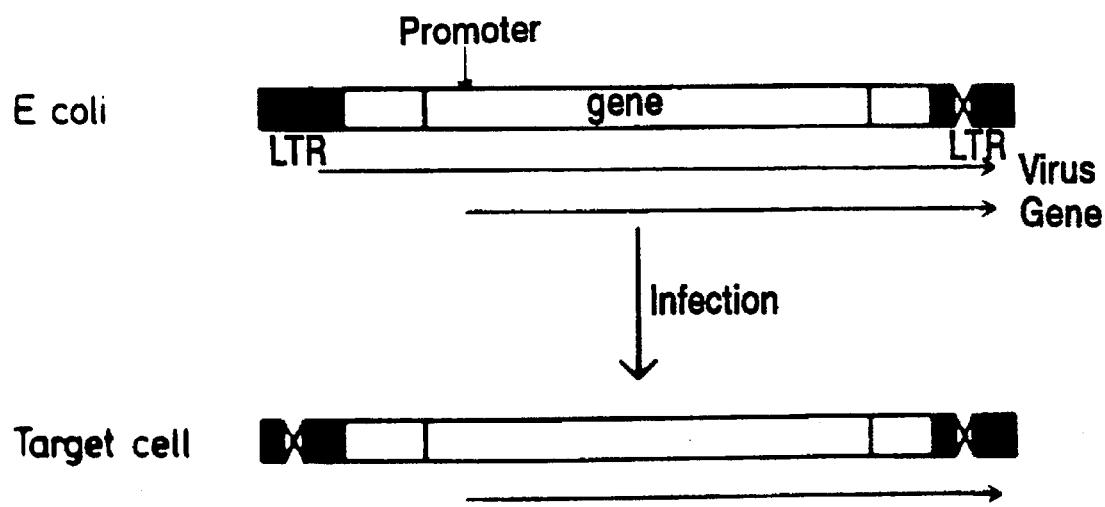

In a DC vector the gene of interest is inserted within the U3 region of the 3' situated LTR by using standard recombinant DNA techniques. The gene can be inserted in either of two transcriptional orientations as indicated by the two arrows. Also shown is the viral RNA which is initiated at the border of U3 and R regions of the 5' LTR and terminates at the border of R and U5 in the 3' LTR. Consequently, the gene inserted into the 3' LTR is present within the retroviral transcriptional unit. The DNA construct is then converted into virus and introduced into the target cell as shown in FIG. 1. In the target cell the U3 region of the 3'LTR, including the inserted gene is "transferred" to the 5' LTR as shown, thus generating two copies of the inserted gene. As a result of this duplication, the gene present in the 5'LTR is now outside the retroviral transcriptional unit.

FIG. 5 parts A and B. A DC vector containing the ADA minigene.

The ADA minigene consists of the ADA promoter fused to the ADA cDNA (20,21) which was inserted downstream to the Neo gene of the N2 vector to generate the AAX vector shown in panel A. To generate the DCA vector shown in panel B, the N2 vector was first modified by the insertion of a polylinker cloning site into the NheI site present in the U3 region of the 3' LTR, between the distal end of the LTR and the viral enhancer (called N2A). The ADA minigene was then inserted into a SnaBI site present in the polylinker. For additional details see (1) and text.

Figure 6:
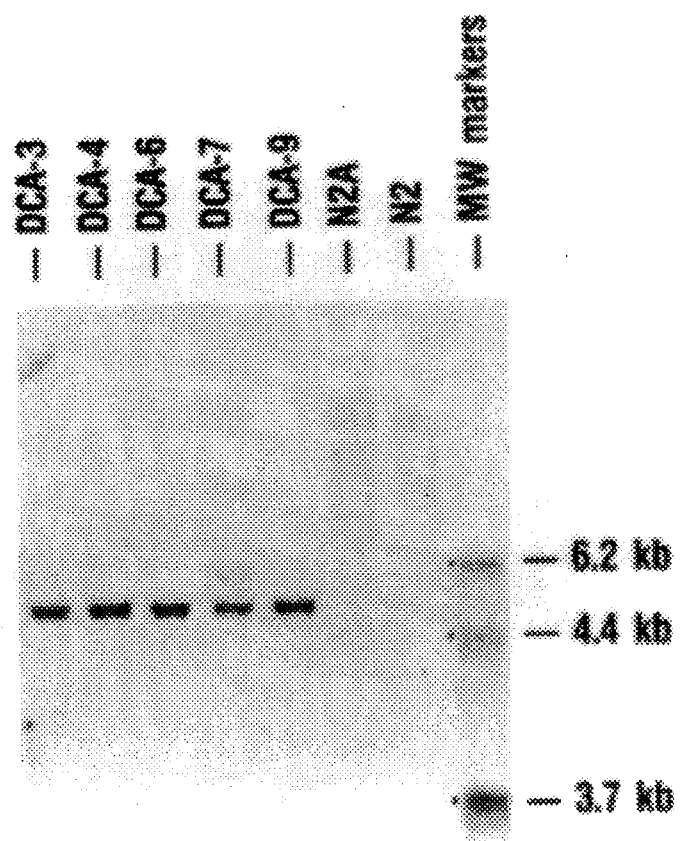

FIG. 6. DNA analysis of NIH 3T3 cells infected with DCA virus.

$10^3$ infectious units of DCA virus from 5 producer lines was used to infect $2\times10^5$ NIH 3T3 cells. Infected cells were selected in G418, expanded and cellular DNA was isolated. DNA was digested with Bam HI, subjected to electrophoresis in 1% agarose gels and blotted to nitrocellulose paper. Vector specific DNA was detected by hybridization with a Neo specific probe. Molecular weight markers constitute a mixture of three DNA fragments of known molecular weights of 6.2, 4.4 and 3.7 kb, containing Neo sequences. N2A is a modified N2 vector as described in FIG. 5. Both N2 and N2A do not contain a Bam HI site. DCA- 3, 4, 6, 7, and 9 are five independently derived virus supernatants obtained by transfection of PA317 cells and isolating single colonies.

FIG. 7 parts A–C. Expression of vector specific RNA in NIH 3T3 cells infected with DCA and AAX virus.

Panel 7A shows the structure of AAX and DCA proviruses and corresponding RNA transcripts (arrows). In the AAX vector the ADA minigene was cloned between the two LTRs (downstream from the Neo gene) and therefore the structure of the provirus is identical to the vector DNA. In the DCA vector the ADA minigene was inserted into the 3' LTR and therefore the provirus will contain two copies of the ADA minigene in each LTR. Three RNA transcripts are expressed from the AAX provirus, two LTR initiated RNA forms unspliced and spliced, and a third RNA transcript expressed from the internally placed ADA promoter which serves as the mRNA for ADA synthesis. The DCA provirus also generates the same three transcripts except that both ADA minigenes can serve as templates for ADA mRNA synthesis. The predicted (see text) and observed (panel B) levels of RNA transcripts in cells infected with DCA virus is indicated by the thickness of the arrows.

Panel 7B shows the RNA blot analysis of cells infected with AAX and DCA virus containing supernatants. Polyadenylated RNA, fractionated on formaldehyde-agarose gels and blotted to nylon filters was first hybridized to an M-MuLV U3 specific probe. After hybridization, exposure and development of the X-ray sensitive film, the probe was removed and filter was rehybridized with a human ADA specific probe. In order to obtain a quantitative comparison of RNA loaded in each lane, the same filter was also hybridized to a human glyceraldehyde-3-phosphate dehydrogenase (GAPDH) probe. AAX-11, DCA-18 and DCA-4 are three independently derived virus preparations which were characterized by DNA blotting to generate the predicted proviruses in the infected cells. V and N are LTR initiated transcripts, the unspliced virion RNA (V) and spliced neo mRNA (N). ADA—the ADA promoter initiated RNA transcripts, R?, X, a and b are additional transcripts whose possible origin is discussed in the text.

Panel 7C shows the results of another experiment, as described in Panel 7B (see text for additional details).

Figure 8:
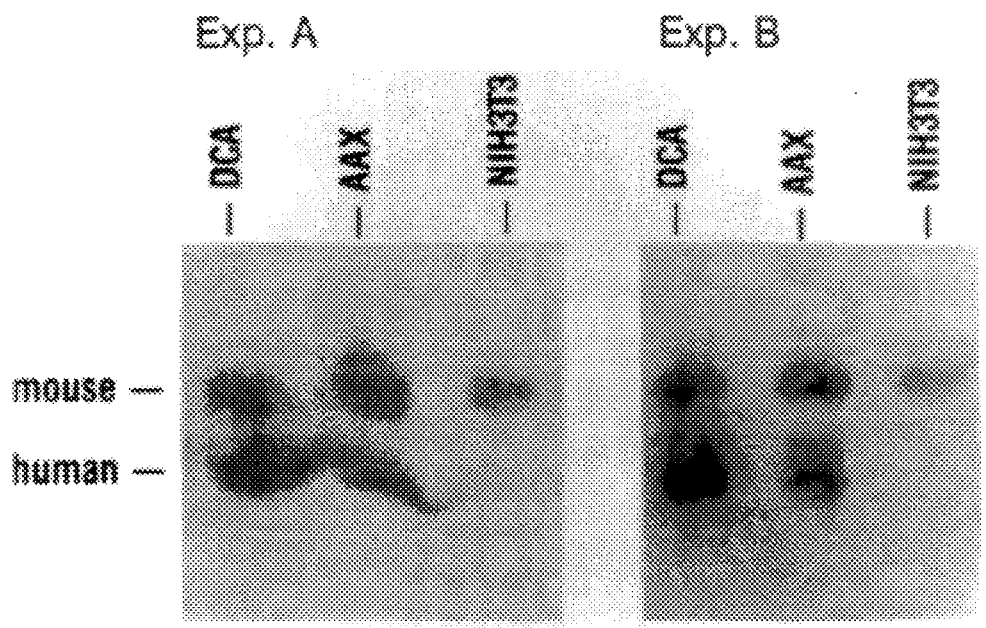

FIG. 8. Human ADA enzyme activity in NIH 3T3 cells infected with DCA and AAX virus.

The presence of the human and ADA mouse isozyme in NIH 3T3 cells was determined by cellogel electrophoresis of cell extracts followed by in situ chemical staining for the ADA enzymatic activity (17, 31).

Figure 9:
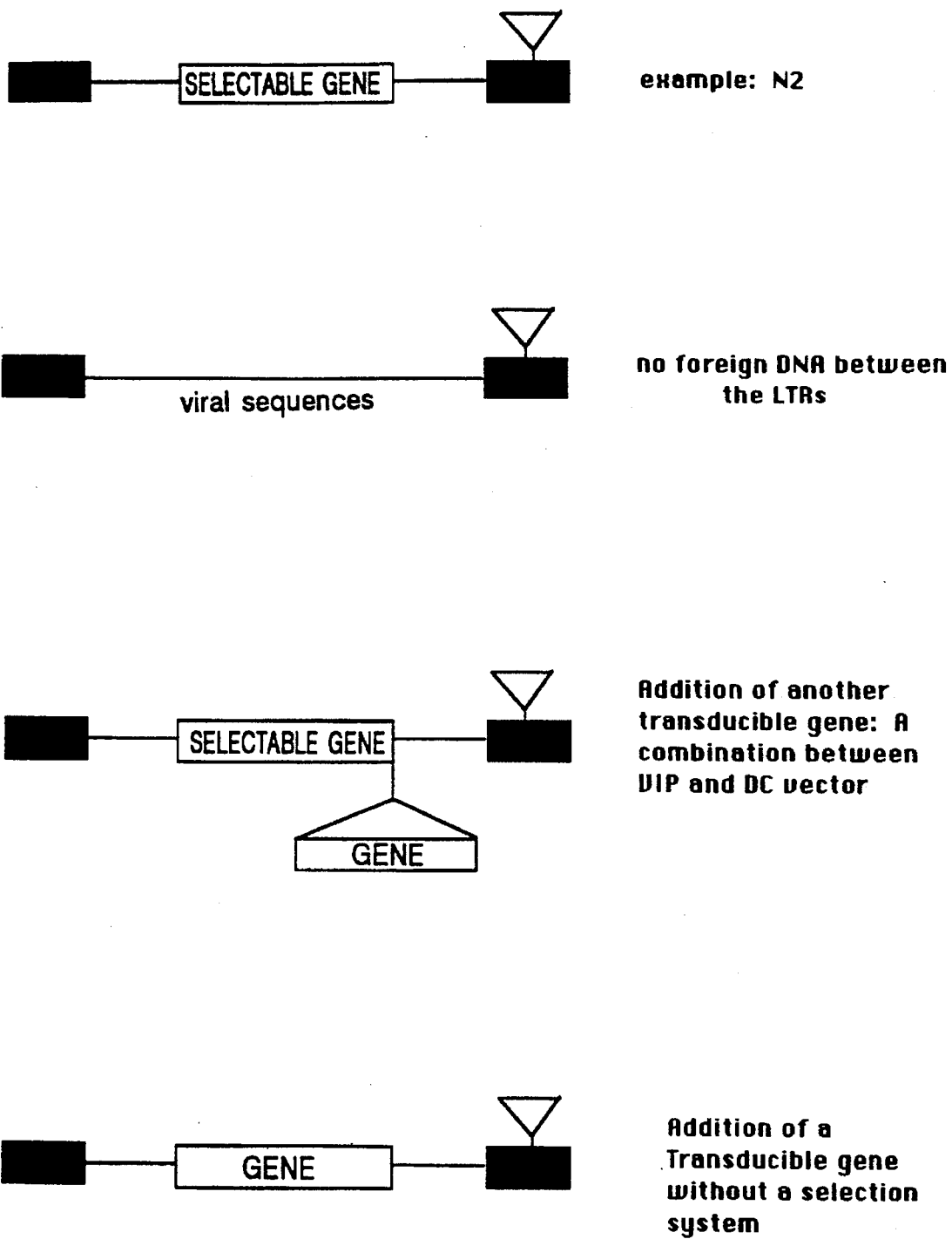

FIG. 9. Schematic diagrams of some of the variations on the sequences that may be present between the two LTRs of DC vectors. (For a more comprehensive but not complete list, see Temin 1986, (18)).

Figure 10:
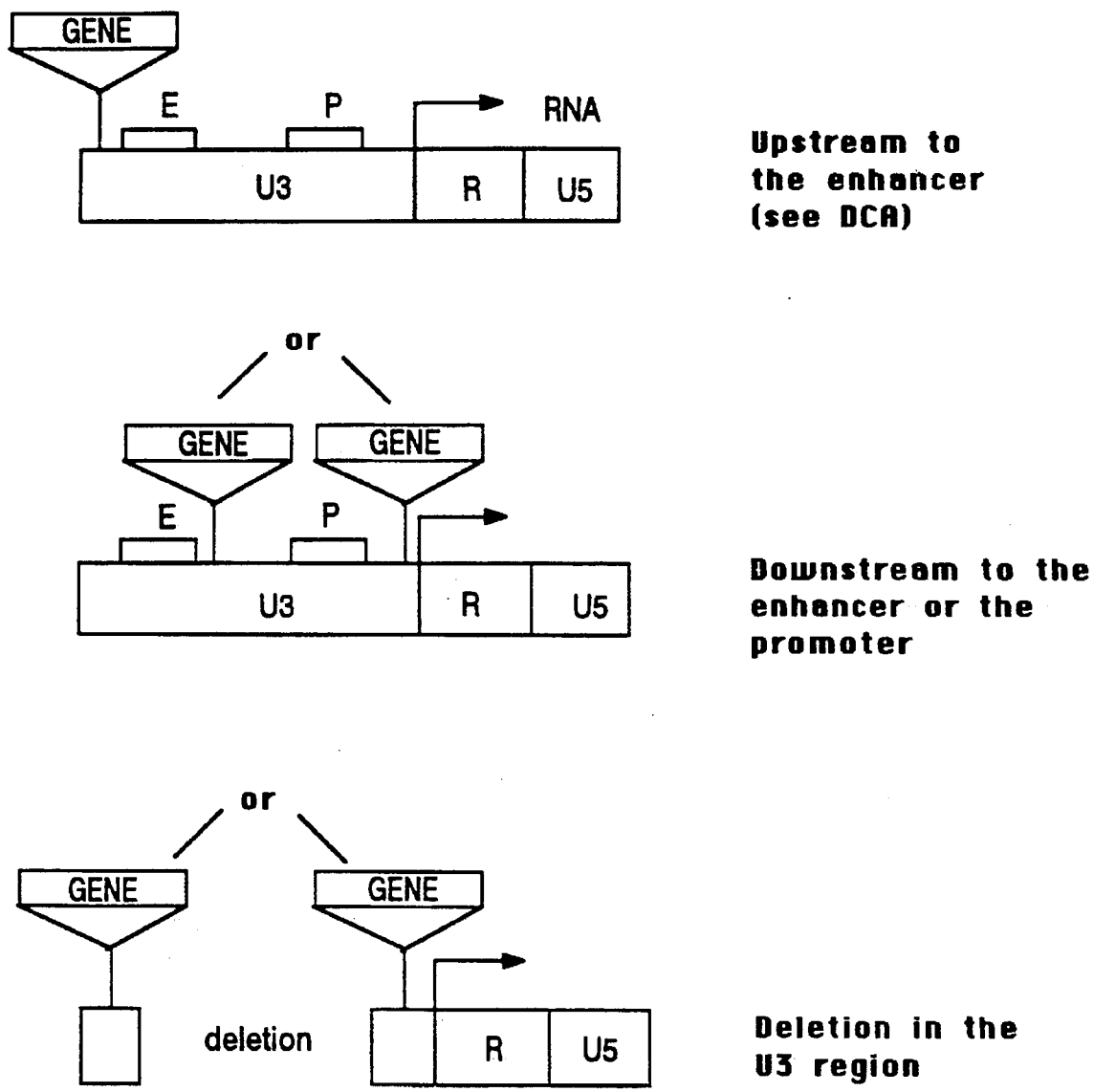

FIG. 10. Modes of insertion into the 3' LTR.

FIG. 11 parts A and B. DNA analysis of NIH 3T3 cells infected with DCA virus.

Panel 11A shows the structure of the DCA vector (recombinant DNA) and the predicted structure of the corresponding provirus in the infected (target) cell. Black boxes represent the viral LTRs, solid lines represent unique viral sequences and open boxes represent the foreign genes introduced into the retroviral vector, the Neo and ADA minigenes. Restriction sites used in this analysis are also shown. N-NcoI; Bg-BglII; B-BamHI; S-StuI. The predicted DNA fragments generated by digestion of the proviral DNA with each restriction enzyme is shown and the size in kilobase-pairs is indicated only for the DNA fragments which hybridize with the Neo probe. FIG. 11B shows the results of a DNA blot analysis of NIH 3T3 cells infected with DCA virus containing supernatants.

Panel 11B shows that hybridization was performed with a Neo specific probe. Lane 1—uninfected NIH 3T3 cells. Lane 2–5, DCA-6 virus supernatant infected cells digested with StuI (lane 2), NcoI (lane 3) BglII (lane 4) and BamHI (lane 5). Lanes 6–8, cellular DNA digested with BamHI, derived from NIH 3T3 cells infected with three additional virus containing supernatants. DCA-3 (lane 6); DCA-4 (lane 7); DCA-9 (lane 8). MW—Migration of DNA fragments generated by HindIII digestion of A DNA is indicated in kilobase-pairs.

FIG. 12. HUT 78 and Raji cells infected with AAX and DCA virus.

$5\times10^5$ HUT 78 and Raji cells were infected with AAX or DCA virus in one milliliter of culture and grown for 48 hours before G418 was added to a concentration of 0.75 mg/ml and cells were cultured for about two weeks until control cultures did not contain live cells. An M-MuLV U3 specific probe was used to detect vector specific RNA transcripts. The putative ADA transcript present in Raji cels infected with AAX virus can be seen upon longer exposure of the X-ray film (not shown). A band migrating at approximately the same position in HUT 78 cells infected with AAX virus does not correspond to the ADA transcript.

Figure 13:
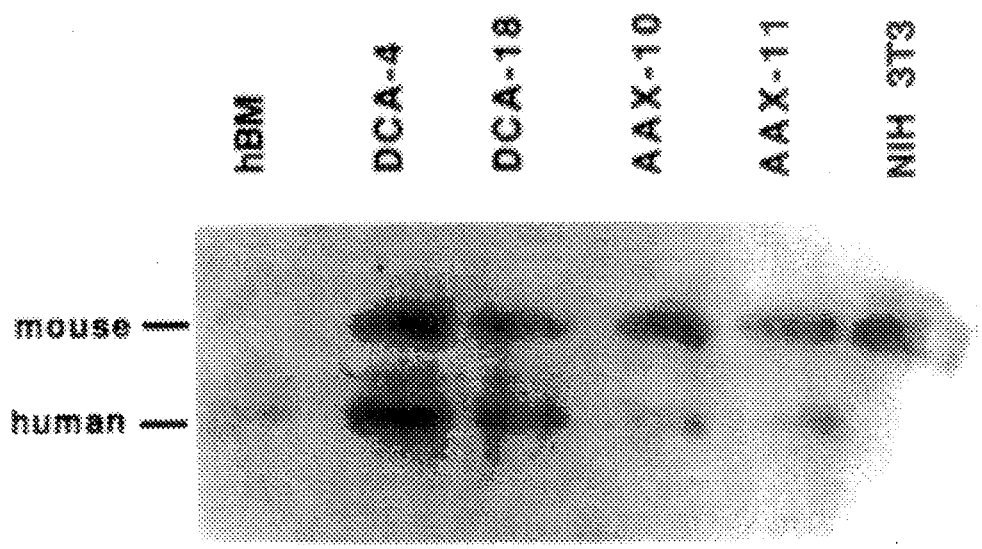

FIG. 13. NIH 3T3 cells infected with AAX or DCA virus.

Cell extracts prepared from NIH 3T3 cells infected with AAX or DCA virus were subjected to electrophoresis in a cellogel matrix and the migration of mouse and human ADA isozymes was determined by a histochemical staining procedure (17,31). DCA-4, DCA-18, AAX-10 and AAX-11 are independently derived virus preparations. Extracts prepared from uninfected NIH 3T3 cells and human bone marrow (hBM) were used to distinguish between the endogenous mouse isozyme and the vector transduced human isozyme, respectively.

DETAILED DESCRIPTION OF THE INVENTION

This invention concerns a retroviral vector for introducing into a eucaryotic cell DNA encoding a transcription unit comprising a first DNA sequence which is the reverse transcript of at least a portion of a retrovirus, said portion including both the 5' LTR sequence and the 3' LTR sequence of the retrovirus, and a second DNA sequence encoding the transcription unit, and which is inserted into the U3 region of the 3' LTR sequence. The transcription unit may be virtually any DNA sequence capable of being transcribed into RNA, regardless of whether such RNA is subsequently translated into a polypeptide, for example, an antisense RNA sequence, i.e., a sequence which complementary to all or a portion of another RNA molecule present in the host cell.

Those skilled in the art will recognize that a number of retroviruses may be employed to construct the retroviral vector of this invention. Among such retroviruses are avian sarcoma viruses (AvSV), murine sarcoma viruses (MuSV), and leukemia viruses such as murine leukemia viruses, e.g., mouse Moloney leukemia virus (M-MuLV). Particularly useful as a retroviral vector in the practice of this invention is the mouse Moloney leukemia virus (M-MuLV).

In one embodiment, the first DNA sequence is the reverse transcript of the entire retrovirus. In another embodiment the first DNA sequence is the reverse transcript of a portion of the retrovirus, said portion including both the 5' LTR sequence and the 3' LTR sequence of the retrovirus. Useful as the first DNA sequence in the practice of this invention is the retroviral vector N2.

In a further embodiment, the second DNA sequence encoding the transcription unit encodes the human ADA minigens. In another embodiment, the second DNA sequence encoding the transcription unit encodes a binding sequence corresponding to a eucaryotic promoter for any of polymerase I, polymerass II, or polymerass III. It is known to those skilled in the art that eucaryotic polymerase I transcribes ribosomal genes; that eucaryotic polymerass II is responsible for the expression of the protein coding cellular genes; and that eucaryotic polymerass III transcribes the 5S and t-RNA genes of cell. In a still further aspect of this invention, the second DNA sequence encoding the transcription unit encodes a binding sequence corresponding to a procaryotic polymerass, such as T7 polymerass.

The second DNA sequence encoding the transcriptional unit also may encode an RNA sequence, such as antisense RNA or mRNA, or encode a polypeptide of interest. The antisensene RNA may be an RNA sequence which is complementary to a nucleotide sequence encoded by a pathogen, such as a bacteria, parasite or virus, e.g. the Human Immunodeficiency Virus (HIV). The second DNA sequence encoding the transcription unit also may encode an RNA which is the recognition sequence for the DNA or RNA binding protein. The polypeptide encoded by the second DNA transcription unit may be, but is not limited to encoding mammalian polypeptides or proteins, such as the hemoglobin protein. The second DNA sequence encoding the transcription unit also may encode a selectable or identifiable phenotypic trait, such as resistance to antibiotics, e.g. ampicillin, tetracycline, and neomycin, or may comprise a non-selectable gene.

Another feature of this invention is a retroviral vector further comprising a non-retroviral DNA sequence present between the 5' and 3' LTRs of the retrovirus vector. This non-retroviral DNA sequence may encode a selectable or identifiable phenotypic trait. Such a trait may be resistance to antibiotics, e.g., ampicillin, tetracycline, and neomycin. In another aspect, this additional sequence may comprise a non-selectable gene. (For examples of such see FIG. 9 and Temin, 1986 (18)).

One embodiment of this invention concerns a retroviral vector wherein the second DNA sequence encoding a transcription unit is inserted into the U3 region of the 3' LTR sequence. In accordance with the practice of this invention, the second DNA sequence encoding the transcription unit may be inserted at any location within the U3 region of the 3' LTR, or alternatively, may be inserted upstream of the enhancer and promoter sequences within the U3 region of the 3' LTR. In another, the second DNA sequence is inserted at the U3 region of the 3' LTR sequence downstream of the enhancer sequence. In still another embodiment, the second DNA sequence is inserted into the U3 region of the 3' LTR sequence, in particular downstream of the promoter sequence. Another feature of this invention is a retroviral vector, described above, wherein the enhancer and/or promoter of the U3 region of the 3' LTR have been deleted or mutated, e.g. by mutation.

Methods used in preparing the retroviral vector of the present invention are known in the art and are described more fully hereinafter under Experimental Details and Discussion.

Additionally, this invention provides a method of producing a virion useful for introducing into a eucaryotic cell DNA encoding a transcription unit comprising transfecting the retroviral vector described above, into a suitable packaging cell line under conditions such that the virion is formed within, and excreted by, the packaging cell line. This invention also concerns a virion produced by such a method.

Methods for producing the virion in accordance with this invention are also known to those skilled in the art, as will be exemplified in the Experimental Details and Description Section.

This invention also provides a method of introducing into a eucaryotic cell a DNA transcription unit which comprises infecting the cell with a virion produced by the method described above under conditions such that the DNA transcription unit is incorporated into the chromosomal DNA of the eucaryotic cell. In one embodiment the eucaryotic cell is a mammalian cell, e.g., a hemopoietic stem cell.

Methods of infection and methods of detecting the presence of the products of transcription units or genes, i.e., DNA encoding a polypeptide or protein of interest, are also well known in the art, as exemplified in the next section.

This invention is illustrated in the Experimental Details and Discussion sections which follow. These sections are set forth to aid in an understanding of the invention but are not intended to, and should not be construed to, limit in any way the invention as set forth in the claims which follow thereafter.

PRINCIPLE OF DOUBLE COPY (DC) RETROVIRAL VECTORS

The following section describes the retroviral vector design of the present invention which is useful for the expression of the transduced gene, by eliminating the interference from the retroviral read, brought transcript, emanating from the retroviral LTR. The strategy is distinct and superior to that of SIN vectors.

DC vectors utilize the same principle used in the design of SIN vectors, i.e. that sequences in the 3' LTR of one provirus (the U3 region) are "transferred" to both LTRs of the progeny provirus (23). In SIN vectors this principle was utilized by introducing a deletion in the U3 region of the 3' LTR to eliminate the enhancer and promoter sequences thus inactivating the viral transcriptional unit. This principle also was exploited for the transduction of a procaryotic t-RNA suppressor gene in replication competent retroviruses for the purpose of selection in bacterial cells and not for the expression of transduced genes in eucaryotic cells. The insertion of the t-RNA gene into the U3 region of the LTR was done to avoid the disruption of essential retroviral genes, not in order to exploit the duplication event associated with this process (12, 16).

In SIN vectors, VIP type vectors and in fact in all retroviral vectors constructed so far, the transduced gene, i.e., the gene whose expression in the eucaryotic cell is sought, is always placed in between the two LTRs and, therefore, its position relative to the two LTRs will not change in the infected cell. The unique feature of DC vectors, as illustrated in FIG. 3, is that the transduced gene is placed within the U3 region of the 3' LTR. FIG. 4 shows that in an infected cell the gene is transferred also to the 5' LTR, generating two copies of the transduced gene, hence its name, double copy vector. The important result is that in its new position, in the 5' LTR, the gene is physically placed outside the retroviral transcriptional unit, eliminating or at least reducing the negative effects of the retroviral transcriptional unit (FIG. 4).

N2 BASED DC VECTORS FOR THE TRANSDUCTION OF MINIGENES

This section describes a specific DC vector to illustrate the vector design principle in accordance with the present invention. This particular vector is based on the high titer N2 vector and it contains the human ADA minigene. The 2082 base pairs (bp) long ADA mini-gene consists of the ADA promoter which extends 730 bp upstream from the RNA start site, and the ADA coding sequences from which the polyadenylation signal sequence, AAUAAA, was removed (20, 21). The ADA minigene was inserted into the 3' LTR of the N2 vector in a transcriptional orientation which is parallel to the viral transcriptional unit. Characterization of this vector described below demonstrates that DC vectors function as predicted and also illustrates the additional benefits of this particular version of DC vector design.

Figure 5A:
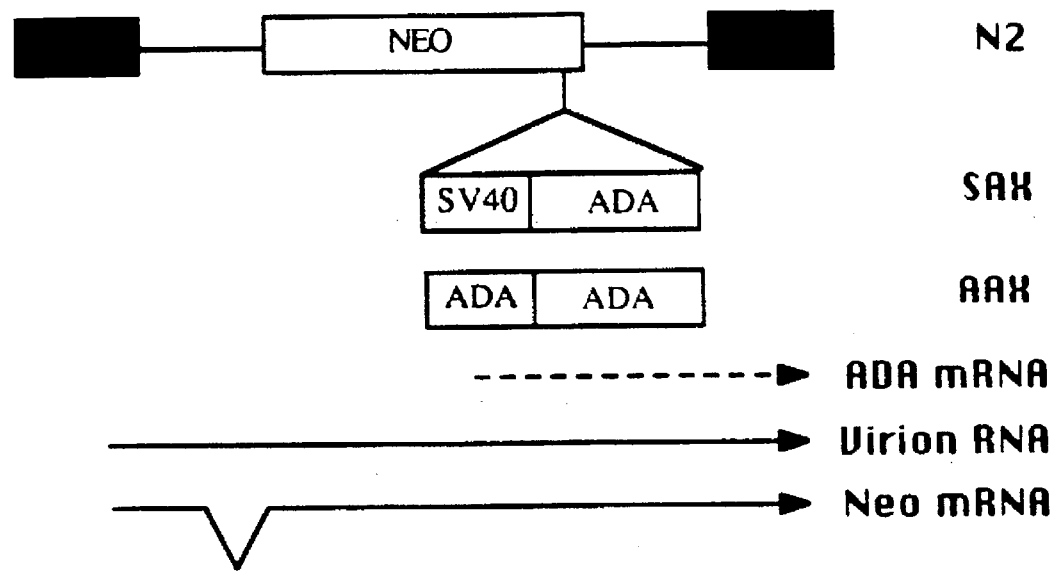

VIP vectors carrying minigenes are frequently used in studies involving retroviral gene transfer. This strategy has been used for the transduction of the human ADA gene (1,11). As shown in FIG. 5A, in these studies the high titer N2 vector was used and the ADA minigene was inserted downstream to the Neo gens between the two LTRs.

In one construct, the early SV40 promoter was fused to the human ADA cDNA (SAX). This vector was used to express the ADA gene in mouse fibroblast cells (1), established human lymphold cells (11) and bone marrow cells from ADA deficient patients (Bordignon et al. PNAS, in press). More recently a new vector was constructed and used in studies by Bordignon et al. (PNAS, in press) in which the ADA cDNA is fused to its own promoter (AAX) which is equally active but not superior to the SAX vector, also as shown in FIG. 5A. FIG. 5A also shows the structure of the SAX and AAX vectors and the corresponding RNA transcripts present in the vector infected cells. Note that the structure of the vector DNA as constructed in vitro, is identical to the structure of the provital DNA in the infected cell. The two long transcripts generated from SAX or AAX are initiated in the 5' LTR from the retroviral promoter and terminate in the 3' LTR which contains the polyadenylation signal. The unspliced RNA species is the virion RNA and the spliced form serves as the mRNA for the expression of the Neogene. The shorter transcript, the mRNA for the ADA gene is initiated within the internal promoter, SV40 or ADA, and because the minigene lacks a polyadenylation signal, the transcripts terminate in the viral 3' LTR at the same site which is used by the LTR derived transcripts. The internal ADA mRNA is represented by a dotted line to illustrate the fact that the level of expression of internally promoted transcripts is unpredictable and often low. (For more details see Armentano et al., 1987 (1)).

Figure 5B:
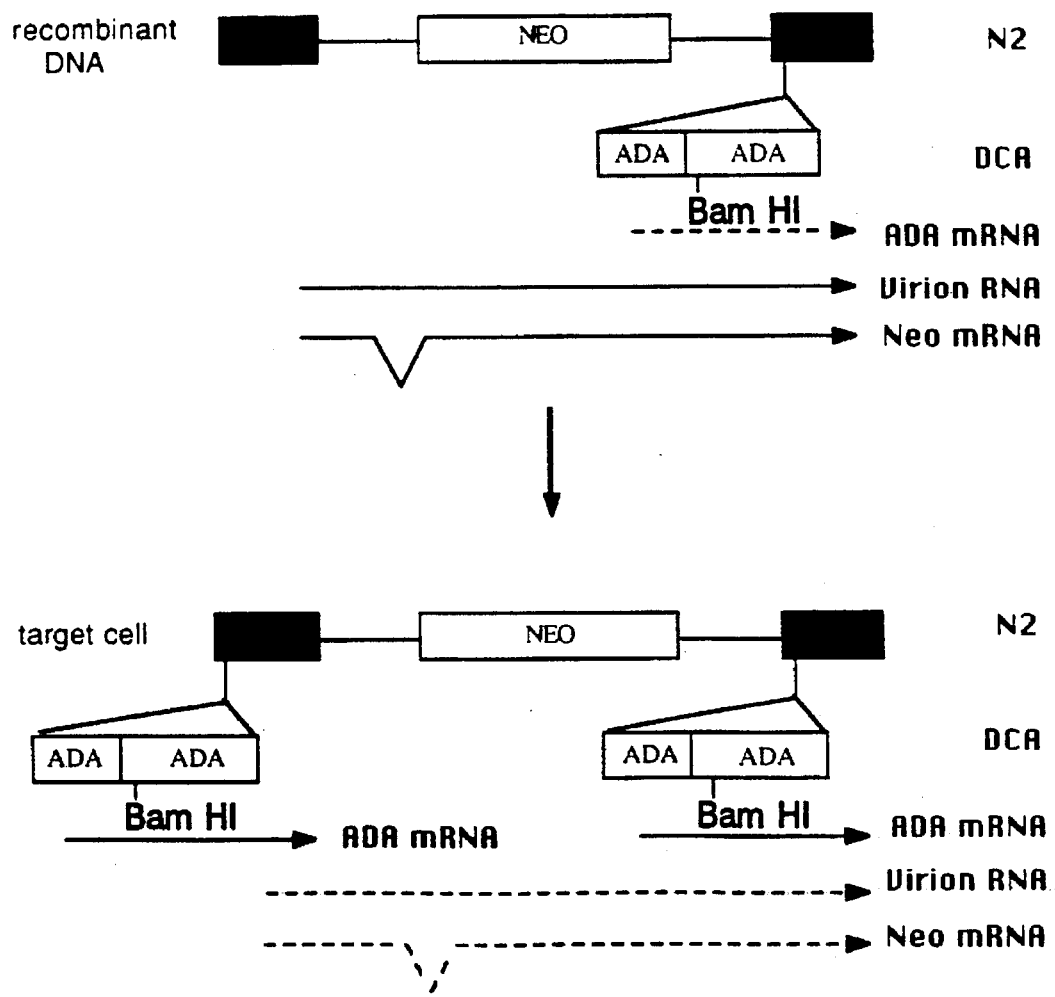

The structure of a DC vector carrying the ADA minigene called DCA, is shown in FIG. 5B. This particular vector based on the N2 vector and the human ADA minigene which was inserted into the U3 region of the 3' LTR, upstream to the vital enhancer. To construct the DCA vector, the N2 vector was first modified by insertion of a 52 bp long polylinker sequence into an NheI site present in the 3' LTR, 30 bp downstream from the 5' end of the 3' LTR. The polylinker sequence contains five restriction sites which are unique to the N2 plasmid: ApaI, BglII, SnaBI, SacII and MluI. Since the insertion of the polylinker sequence into the NheI site may interfere with viral integration, the polylinker sequence was designed to regenerate an additional 16 bp of viral sequence downstream from the NheI site. Thus, the polylinker modified N2 vector, called N2A, contains a total of 50 bp of viral sequence downstream from the 5' end of the LTR before foreign sequence is encountered. The ADA minigene was inserted into the unique SnaBI site present in the polylinker.

As in AAX, because the ADA minigene lacks a polyadenylation signal, the ADA transcripts also will utilize the viral polyadenylation signal and terminate at the same site used by the LTR transcripts. This feature, the lack of polyadenylation signal in the transduced gene and the consequent use of the retroviral signal, endows this subset of DC vectors with additional useful properties, described below.

FIG. 5B shows that in the infected cell, i.e., the target cell, the ADA minigene will have been transferred also to the 5' LTR, the immediate result being the duplication of the transduced gene in the infected cell (see also FIG. 4). The most important consequence of this duplication, basic to the design of DC vector, is that the ADA minigene copy in the 5' LTR is present outside the retroviral transcriptional unit and, therefore, its activity will be less affected by a retroviral readthrough transcriptional unit.

As indicated in FIG. 5B, this particular DC vector contains a minigene which utilizes the viral polyadenylation signal. This is true not only for the 3' LTR situated minigene but it also holds true for the 5' LTR contained minigene in the infected cell which utilizes the polyadenylation signal encoded in the 5' LTR. FIG. 5B also illustrates the fact that initiation of RNA transcription as defined by the border between U3 and R regions in LTR precedes the polyadenylation site as defined by the border between R and U5 regions. Therefore, the ADA gene transcript in the 5' LTR will partially overlap with the retroviral transcriptional unit through region R. In other words, with the transfer of the ADA transcriptional unit to the 5' LTR, the retroviral transcriptional unit and its expression should be inhibited. This is indicated in FIG. 5B where the viral transcripts are represented by dotted lines. If so, it is reasonable to expect that the inhibitory effect of the retroviral transcriptional unit on the 3' LTR situated ADA transcript will be also relieved as indicated by the fact that the 3' situated ADA minigene is now represented in the infected cell by a bold line. This is indeed the case as shown in FIG. 7. Probably the most significant consequence of eliminating or decreasing the activity of the viral transcriptional unit is a parallel reduction in the occurrence of recombination events leading to the formation of replication competent retroviruses, a major concern associated with the use of retroviruses for human therapy.

TRANSFER AND EXPRESSION OF THE ADA GENE USING THE DCA VECTOR

This section provides experimental evidence on the function and charateristics of the DC vectors, exemplified by the DCA vector shown in FIG. 5B, in accordance with the present invention.

TRANSFER OF THE ADA MINIGENE TO THE 5' LTR—THE DUPLICATION PROCESS

The construction of the DCA vector and derivation of the corresponding virus was achieved following established procedures. Briefly, the recombinant DNA carrying the ADA minigene was generated by standard recombinant DNA techniques and converted to a retroviral virion in the following procedure. PA317 packaging cells (13) were transfected with the DCA DNA, grown in medium containing 0.7 mg/ml G418 to select for cells expressing the Neo gene contained within the DCA vector), G418 resistant colonies were isolated and expanded to cell lines. The supernatant of each cell line was then tested for the presence of DCA virus. First, the titer of virus was determined by infecting NIH 3T3 cells with serial dilutions and growing cells in the presence of G418. 3 out of 10 cell lines generated high titers of Neo containing virus, $2 \times 10^4 - 1.0 \times 10^5$ Neo cfu/ml. In this experiment, a titer AAX virus supernatant (see FIG. 5A) used as a control yielded $2\times10^5$ cfu/ml. Thus, it can be concluded that the DCA vector yields high titers of virus which is characteristic of N2 based vectors.

Next it was determined whether the ADA minigene was duplicated in the infected cells, as shown in FIG. 5B. In order to do this, the DNA content of the NIH 3T3 cells infected with the high titer DCA supernatants was analyzed by DNA blotting. Chromosomal DNA was prepared using the guanidium isothiocyanate extraction procedure (24). DNA was digested with various restriction enzymes, subjected to electrophoresis in 1% agarose gels (10ug per lane), transferred to a nylon filter (Biotrans, ICN) using an electroblotting apparatus (BioRad), hybridized with a $^{32}$P-labelled specific probe and exposed to an X-ray sensitive film (Kodak XARS) in the presence of intensifying screens (Dupont Cronex lighting plus).

Figure 11A:
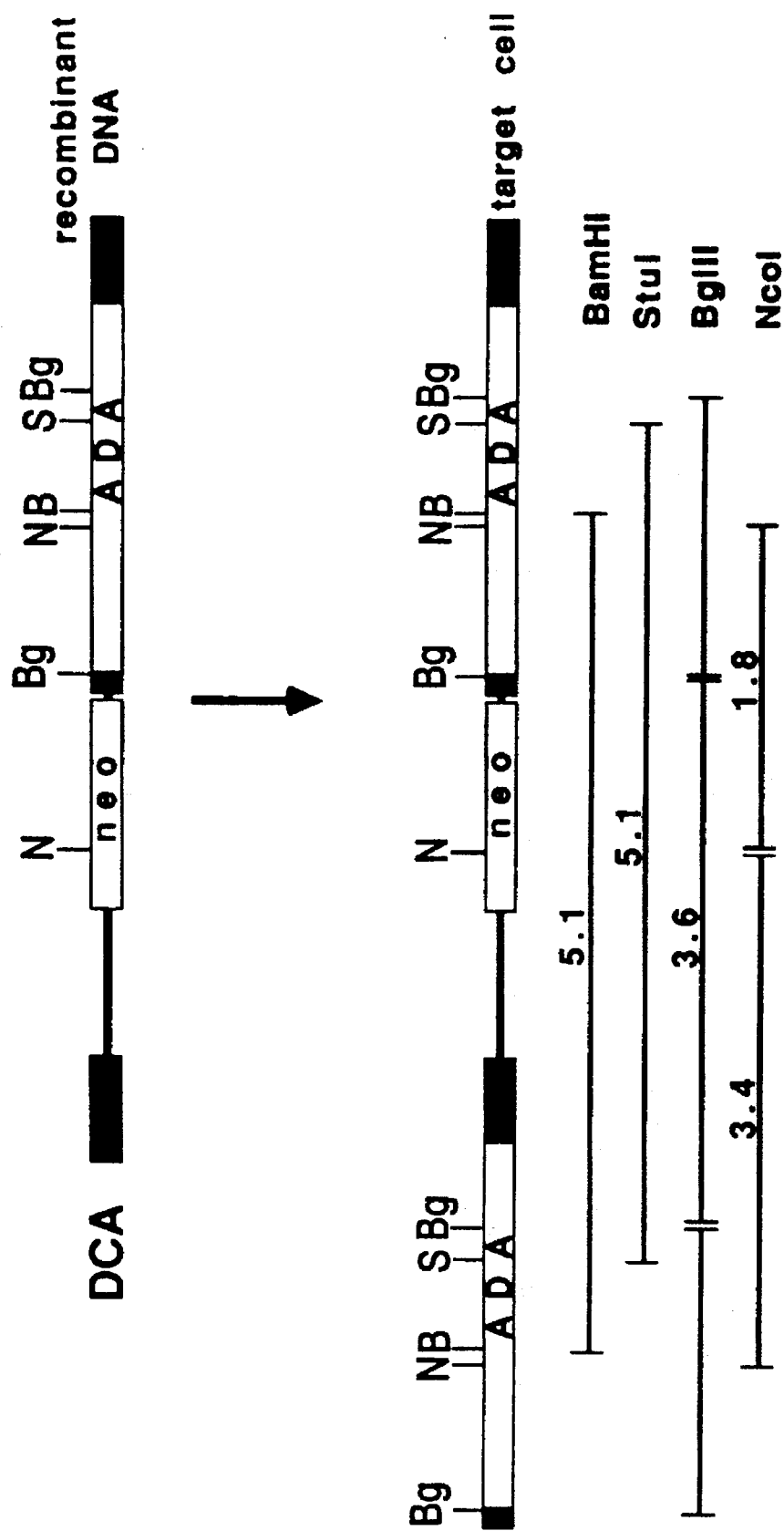
Figure 11B:
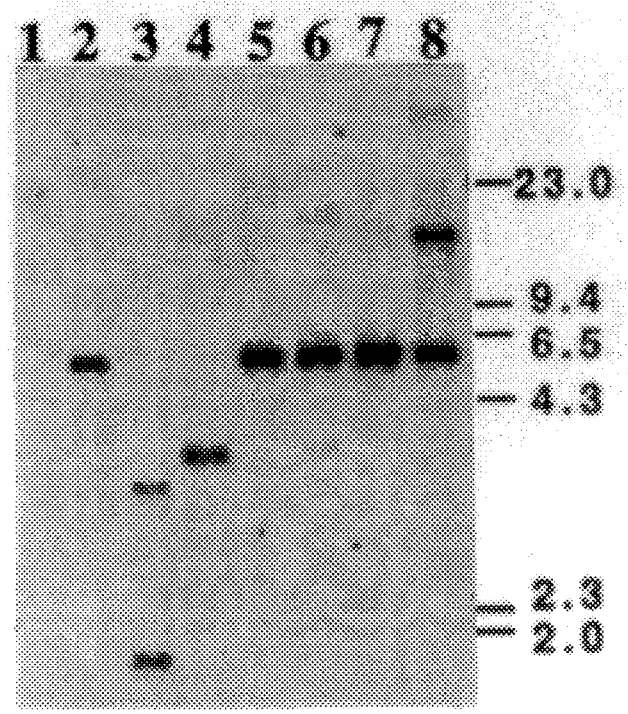

FIGS. 6 and 11 show the DNA analysis of NIH3T3 cells infected with DCA virus. FIGS. 5B and 11A show that the DCA DNA construct contains one Bam HI site in the ADA minigene present in the 3' LTR. If the ADA minigene is transferred to the 5' LTR, a characteristic BamHI DNA fragment will be generated in the infected cells, about 5.1 kb long. Indeed, when NIH 3T3 cell DNA, infected with DCA virus, is digested with Bam HI, a DNA fragment of the expected size is generated in each case, as shown in FIGS. 6 and 11B.

As noted above, FIG. 11A shows that a single BamHI restriction site is present in the DCA vector DNA, and if the 2.7 kb hybrid LTR is duplicated at the 5' end of the proviral DNA, a characteristic 5.1 kb DNA fragment hybridizing to the Neo probe, will be generated in the infected cells. As shown in FIG. 11B, lanes 5–8, infection of NIH 3T3 with four independently derived DCA virus containing supernatants generates the predicted 5.1 kb DNA band. Additional bands present in lanes 6 and 8 indicate that the corresponding virus preparations also contain virus which has undergone rearrangements, presumably during transfection of the PA317 cells with the vector DNA. Restriction analysis using restriction enzymes StuI, BglII, and NcoI is also consistent with the accurate duplication of the hybrid 3' LTR in the infected cells (FIG. 11B lanes 2, 3, 4 and accompanying diagram in FIG. 11A).

EXPRESSION OF THE ADA MINIGENE IN NIG 3T3CELLS INFECTED WITH DCA AND AAX VIRUS

Expression of the ADA minigene in the infected cells was determined by analyzing (a) the presence of vector specific RNA transcripts in the cell and (b) appearance of enzymatic activity corresponding to the human ADA gene product. Total cellular RNA (both nuclear and cytoplasmic) were prepared using the guanadium isothiocyanate extraction procedure (24). Total cellular RNA was fractionated on oligo (dt) cellulose columns, the poly A$^+$RNA fraction was subjected to electrophoresis in 1% agarose-formaldehyde gels, (25) and vector specific RNA species were identified after electroblotting to nylon filters, hybridization with $^{32}$P-labelled probes and exposure to X-ray sensitive film in the presence of intensifying screens. In these experiments, the expression of the ADA gene from the DCA vector was compared to that of AAX, a conventional vector (see FIGS. 7A as well as 5A and 5B).

AAX is similar to the DCA vector, except that the ADA minigene is inserted downstream to the Neogene, 457 bp upstream from the cloning site in the DCA vector. FIGS. 7A and B show the structure of the AAX and the DCA derived proviruses and the predicted RNA species expressed from the viral LTR and the ADA promoter in NIH 3T3 cells. N2 based vectors generate two LTR derived transcripts, an unspliced RNA species and a spliced RNA form (FIG. 7A, virion RNA and Neo RNA, respectively). A third RNA species is expressed from the internal ADA promoter (1). All three RNA transcripts terminate at the polyadenylation site present in the viral LTR, the R/U5 junction. The two LTR initiated transcripts generated from AAX and DCA vectors are identical in size, while the ADA promoter initiated transcript expressed from the DCA vector should be 457 nucleotides shorter than the corresponding transcript synthesized on the AAX template. FIG. 7A also shows that in the DCA provirus a second copy of ADA minigene is present in the 5' LTR, thus generating two ADA transcripts per provirus. If the LTR initiated readthrough transcript inhibits the activity of internal promoters, the placement of the ADA minigene in the 5' LTR will enhance the expression of ADA in cells harboring the DCA provirus as compared to cells harboring the AAX provirus.

Figure 7B:
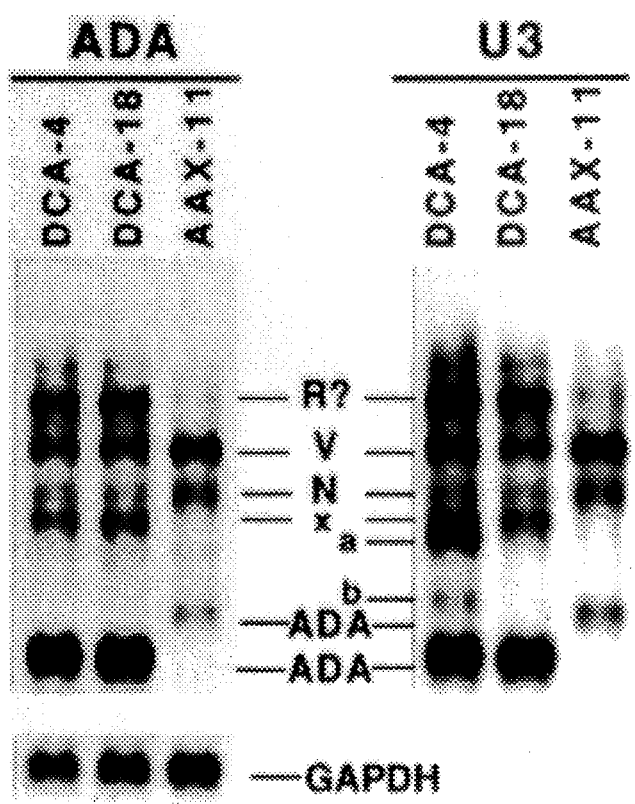

FIG. 7B displays the specific RNA species expressed in NIH 3T3 cells infected with AAX and DCA virus. DCA vector infected cells express 10–20 fold higher levels of ADA promoter initiated transcripts as compared to AAX vector infected cells. (Relative levels of RNA transcripts were determined by exposing the autoradiogram for various times and correcting for the small variations in RNA loaded in each lane). This difference in RNA expression is consistent with the prediction that placement of one copy of the ADA minigene outside the viral LTR will reduce the inhibitory effect of an upstream promoter on the activity of a downstream situated promoter. (It is not possible determine experimentally whether one or both copies of the ADA minigens in the DCA provirus contribute equally to ADA expression). It is also evident from this analysis that in cells infected with DCA virus, expression of the LTR initiated transcripts (FIG. 7B, V and N) is reduced. (The unspliced RNA form (V) is reduced 3–5 fold and the spliced RNA form (N) is reduced 10–15 fold). This is also consistent with the observations that readthrough transcripts inhibit the activity of internal promoters since the ADA promoter initiated transcript in the 5' LTR traverses the vital enhancer/promoter region overlapping with the LTR initiated transcripts over a short region. Although not possible to test experimentally, reduced expression of the LTR initiated transcripts should augment transcription from the 3' situated ADA minigens as well. (This is indicated by the thickness of the corresponding arrow in FIG. 7A.) Additional RNA species also can be detected in the infected cells as shown in FIG. 7B. A slow migrating RNA species in DCA infected cells, designated R? in FIG. 7B may constitute a readthrough transcript initiated from the 5' situated ADA promoter which terminates in the 3' LTR of the provirus. Two RNA species designated a and b, detected only with the M-MuLV U3 probe in cells infected with one DCA virus isolate, comigrate with N2 parental vector generated transcripts (not shown). Most likely these two RNA species reflect a recombination event which occurred between the two LTRs of the DCA vector during transfection of the PA317 cells. Recombination between non identical LTR's in similar circumstances has been previously observed (23). The nature of the RNA species designated X in FIG. 7B which appears in all DCA infected cells, is unclear.

FIG. 7C is another experiment which, like the experiments shown in FIG. 7B, shows that AAX infected cells generate the three expected bands (see FIG. 5A and Armentano et al., 1987 (1)). Bands a and b correspond to the LTR initiated transcripts, the virion RNA and Neo mRNA and band c corresponds to the ADA promoter initiated transcript, the mRNA for the ADA gene product. As shown in FIG. 7C and Judging from the intensity of the three bands, the steady state levels of the three transcripts expressed from the AAX provirus is similar. NIH 3T3 cells infected with the DCA virus also express several vector specific RNA transcripts. In this case, the predominate RNA species (band c*) is the short transcript which corresponds to the ADA promoter initiated ADA mRNA. The viral transcripts initiated in the 5' LTR, although detectable, are present at significantly reduced levels (the two bands in lanes DCA-3 and DCA-6 which migrate slightly slower than bands a and b in the AAX lane).

The conclusions from these experiments are: (1) that the ADA promoter initiated RNA transcript is expressed from the DCA vector. Although it is not possible to quantitate accurately the amount of transcripts produced in AAX and DCA infected cells from this and other experiments, it appears that (1) DCA infected cells.express 10–20 fold higher levels of ADA specific transcripts and corresponding gene product (see also FIG. 8); and (2) it confirms the prediction of the experiment illustrated in FIG. 7C that the transfer of the ADA minigene to the 5' LTR will suppress the synthesis of LTR driven transcripts.

APPEARANCE OF HUMAN ADA ACTIVITY IN NIG 3T3 CELLS INFECTED WITH DCA AND AAX VIRUS

In order to show that infection of cells with the DCA virus leads to the synthesis of a biologically active gene product, infected cells have been analyzed for the presence of ADA enzymatic activity corresponding to the human isozyme. To do this, cell extracts were subjected to electrophoresis in a cellogel matrix under conditions which separate the endogenous mouse ADA enzyme from the human isozyme. Subsequently the cellogel was "stained" for the presence of ADA activity. FIGS. 8 and 13 show that both DCA and AXX infected cells, but not uninfected cells, express the human ADA isozyme in addition to the mouse enzyme, and that DCA infected cells contain higher levels of human ADA enzymatic activity (compare band intensity of human ADA in DCA and AAX lanes relative to the mouse ADA bands, FIGS. 8 and 13).

It was observed that the ADA transcript is poorly expressed in several human lymphold cell lines transduced with the AAX vector such as HUT 78 and Raji (Yu and Gilboa, unpublished results). Therefore, it was of considerable interest to see whether a DC vector design will be more useful in expressing the ADA gene in those cell lines. As shown in FIG. 12, in AAX infected HUT 78 and Raji cells, the internal ADA promoter driven transcripts are barely detectable. On the other hand, substantially higher levels of ADA transcripts are present in cells harboring the DCA vector, providing additional evidence for the potential utility of this type of vector design.

EXPERIMENTAL DISCUSSION

Double copy or DC retroviral vectors were designed in response to the problems which are encountered in expressing retrovirally carried genes. The unique feature of DC vectors is that the foreign gene is inserted within the U3 region of the 3' LTR of the vector resulting in the duplication of the gene and its transposition to the 5' LTR, outside the retroviral transcriptional unit. The utility of the DC vector design was tested using a 2.1 kb long ADA minigene which was inserted into the 3' LTR of the Neo containing retroviral Vector N2. DNA analysis has shown that the 2.7 kb long chimeric LTR was faithfully duplicated in the infected cell (FIGS. 6 and 11). Several studies have described the insertion of short DNA sequences into the 3' LTR of retroviruses, which did not adversely affect viral functions (12, 16, 26). What restrictions may exist on the insertion of foreign sequences in the U3 region of the retroviral LTR? In the course of retroviral replication, duplication of the LTR and its transposition to the 5' end involves an actinomycin D sensitive step in which the reverse transcriptase uses double stranded DNA as template to generate a second copy of LTR (19). There is no evidence to suggest that this step will be significantly affected by the insertion of additional sequences into the LTR. It is tempting to speculate that, with probable exceptions, insertion of foreign sequences into the LTR will be tolerated, provided it does not affect essential viral functions. If so, the limitations on composition and lengths of sequence inserted into the LTR will be the same limitations encountered when foreign genes are inserted into retroviral vectors, the main limitation being the packaging ability of the corresponding RNA into virions, and a second possible limitation may be the stability of proviruses containing long direct repeats (27). For example, the M-MuLV derived DC vector used in this study should accommodate over 6 kb of foreign sequence in the LTR.

The main prediction in the design of DC vectors was that the transposition of the gene to the 5'LTR, outside the retroviral transcriptional unit, will enhance its expression. The experiments summarized in FIGS. 7, 8, 12 and 13 show that expression of the ADA gene from a DC vector is significantly enhanced in the three cell lines tested, NIH 3T3, HUT 78 and Raji. This, and the reduction in LTR initiated transcripts (FIG. 7B), is consistent with previous observations that upstream promoters exert an inhibitory effect on promoters placed downstream (5, 11, 28), and may explain some of the problems encountered in expressing retrovirally carried genes from internal promoters (29, 30).

In previous studies a procaryotic t-RNA gene was inserted into the 3' LTR of a replication competent murine retrovirus, M-MuLV (12, 16). In this case, the t-RNA gene was expressed in bacteria and was used as a selectable marker during molecular cloning in bacteria. Since the t-RNA was of procaryotic origin, it was not intended to function in eucaryotic cells. The study described herein is the first instance where a DNA sequence is inserted into the 3' LTR of a retroviral derived vector, and it is expressed in a eucaryotic cell. Only in eucaryotic cells, and not in bacteria, the unique advantages of inserting genes into the 3' LTR of retrovirus or retroviral derived vectors, is being realized.

Efficiency of gens transfer, the fraction of cells transduced with a retroviral vector, is a function of virus titer. Although the important issue of virus titers has not been fully addressed in these studies, virus titers generated from the DCA vector ($0.2-0.8 \times 10^5$ cfu/ul) were only slightly lower than virus titers generated from the AAX vector ($1-2 \times 10^5$ cfu/ul), and significantly higher than the titer of virus generated from SIN vectors carrying the ADA gene ($0.5-2 \times 10^3$ cfu/ul, (Yu and Gilboa, unpublished results). Both DCA and AAX vectors are based on the high titer N2 retroviral vector (1).

The retroviral vector N2, which also encodes a Neo gens (1) represents an example of a retroviral vector which can be used to construct a DC vector. Other vectors, containing additional non-retroviral sequences present between the two LTRs (selectable and non-selectable genes, cDNAs) can be also used. See FIG. 9 for several examples and Temin, 1986 (18)).

The specific DC vector described in this study, DCA, represents an example of several possible configurations of DC vectors that can be generated. cDNAs, minigenes as well as whole genes can be inserted in either transcriptional orientation, throughout the U3 region, provided it does not interfere with viral functions. Moreover, the principle of SIN and DC vector design can be combined by removing the enhancer/promoter sequences from the chimetic 3' LTR. Each configuration may have unique advantages and limitations and may serve a particular purpose. (See FIG. 10, for examples.)

In summary, the utility of DC vectors was demonstrated using the ADA minigene which was inserted into the 3' LTR of the M-MuLV based N2 retroviral vector. The general usefulness of this vector design will be determined only from the cumulative experience of many who introduce and express genes in cells of interest. Based on the studies reported here and additional preliminary experience from the laboratory, (see Table 1) it is hoped that DC vectors ultimately will improve the ability to express retrovirally transduced genes, and contribute to the solution of the problems encountered in expressing the transduced gene in cultured cells and in particular when introduced into the live animal.

The general usefullness of this new type of retroviral vector is highlighted by recent experiments summarized in Table I in which a wide variety of DNA inserts were introduced into the DC vector as described in this application. Although not always fully characterised as in the case with the ADA vector DCA, the level of success, i.e. obtaining high titer virue and gene expression in target cell, is substantially higher as compared to our previous experience.

Table I summarizes the use of DC vectors for gene transfer.

TABLE I

| Insert[a] | Virus titer[b] | Infect cells[c] | | |
|---|---|---|---|---|
| | | DNA | RNA | Protein |
| TK-hiFN | H | ND | ND | + |
| TK-mIFN | H | ND | ND | + |
| TK-hIL-2 | H | ND | ND | + |
| TK-tax(HTLV-I) | H | + | + | NA |
| SV-DHFR | M/R | + | + | + |
| SV-DHFR-polyA ← | ND | ND | ND | + |
| ADA-polyA ← | ND | ND | ND | + |
| T7-HIV cap | H | + | − | NA |
| Chimeric t-RNA (3X) | H | + | + | NA |

Legends of TABLE I
A. TK-Herves virus simplex thymidine kinase gene promoter and, SV-early SV40 promoter fused to cDNA: hIFN - human gamma interferon, mIFN - mouse gamma interferon, hIL-2-human interleukin, tax (HTLV-I) tax gene of human T-cell leukemia virus I; DHRF mouse dihydrofolate reductase. T7-HIVcap-Bacteriophage T7 promoter fused to a region of the HIV genome in an antisense orientation, chimeric t-RNA (3x) - three chimeric t-RNA genes. All above constructs were inserted into the N2 base DC vector as described for DCA, in a transcriptional orientation parallel to that of the retrovial transcriptional unit. SV-DHFR-poly A- contains a poly A signal and inserted into the DC vector in an opposite orientation as indicated by the arrow. ADA-poly A consists of the ADA minigene described in the DCA vector and a polyadenylation signal, also in an opposite orientation.
B. Virus titer is an important feature of retroviral vector in many cases constituting the limiting factor in their usefulness. H-Hight titer ($10^5$–$10^6$ cfu/ul); M-Medium titer ($10^4$–$10^5$ cfu/um). For comparison the titer of N2 vector is about $2 \times 10^6$ cfu/ul; AAx - $5 \times 5 \times 10^5$ cfu/ul, DCA-$8 \times 10^4$ cfu/ul and SIN derived vector - $10^2$–$10^3$ cfu/ml.

TABLE I-continued

| Insert[a] | Virus titer[b] | Infect cells[c] | | |
|---|---|---|---|---|
| | | DNA | RNA | Protein |

C. Main feature in the characterization of DC based vector in the target cells. DNA - The structure of provirus to show that duplication has occured. RNA - Expression of corresponding RNA protein. Protien - Expression of the gene product (when insert codes for a protein). Human and mouse gamma interferon and hIL-1 were measured by a bioassay and DHFR was measure by the appearance of MTX resistant cells.
ND - not done.
NA - not applicable.

LEGENDS OF TABLE I

A. TK—Herpes virus simplex thymidine kinase gene promoter and, SV-early SV40 promoter fused to cDNA: hIFN—human gamma interferon, mIFN—mouse gamma interferon, hIL-2-human interleukin, tax (HTLV-I) tax gene of human T-cell leukemia virus I; DHFR mouse dihydrofolate reductase. T7-HIVcap-Bacteriophage T7 promoter fused to a region of the HIV genome in an antisense orientation, chimeric t-RNA (3x)—three chimeric t-RNA genes. All above constructs were inserted into the N2 base DC vector as described for DCA, in a transcriptional orientation parallel to that of the retrovial transcriptional unit. SV-DHFR-poly A-contains a poly A signal and inserted into the DC vector in an opposite orientation as indicated by the arrow. ADA-poly A consists of the ADA minigene described in the DCA vector and a polyadenylation signal, also in an opposite orientation.

B. Virus titer is an important feature of retroviral vector in many cases constituting the limiting factor in their usefulness. H-High titer ($10^5$–$10^6$ cfu/ul); M-Medium titer ($10^4$–$10^5$ cfu/um). For comparison the titer of N2 vector is about $2 \times 10^6$ cfu/ul; AAX—$5 \times 10^5$ cfu/ul, DCA-$8 \times 10^4$ cfu/ul and SIN derived vector—$10^2$–$10^3$ cfu/ml.

C. Main feature in the characterization of DC based vector in the target cells. DNA—The structure of provirus to show that duplication has occured. RNA—Expression of corresponding RNA protein. Protein—Expression of the gene product (when insert codes for a protein). Human and mouse gamma interferon and hIL-1 were measured by a bioassay and DHFR was measure by the appearance of MTX resistant cells.

ND—not done.

NA—not applicable.

REFERENCES

1. Armentano, D., Yu, S. F., Kantoff, P. W., von Ruden, T., Anderson, W. F. and Gilboa, E. (1987). Effect of internal vital sequences on the utility zof retroviral vectors. J. Virol. 61: 1647–1650.

2. Bender, M. A., Palmer, T. D., Gelinas, R. E. and Miller, D. A. (1987). Evidence that the packaging signal of moloney murine leukemia virus extends into the gag region. J. Virol 61: 1639–1646.

3. Cepko, C. L., Roberts, B. E., Mulligan, R. C. (1984). Construction and applications of a highly transmissible murine retrovirus shuttle vector. Cell 37: 1053–1062.

4. Coffin, B. R. (1985). Retroviruses as vectors of foreign genes. In RNA Tumor Viruses, Supplement (editors: R. Weiss, N. Teich, H. Varmus and J. Coffin). Cold Spring Harbor Press, pp. 36–73.

5. Cullen, B. R., Lomedico, P. T., Ju, G. (1984) Transcriptional interference in avian retroviruses— implications for the promoter insertion model of leukemogenesis. Nature 307: 241–245.

6. Dougherty, J. P. and Temin, H. (1987). A promoterless retroviral vector indicates that there are sequences in U3 required for 3' RNA processing. Proc. Natl. Acad. Sci. 84: 1197–1201.

7. Gilboa, E. (1986). Retrovirus vectors and their uses in molecular biology. BioEssay 5.

8. Hawley, R. G., Covarrubias, L., Hawley, T. and Mintz, B. (1987). Handicapped retroviral vectors efficiency transduce foreign genes into hematopoietic stem cells. Proc. Natl. Acad. Sci. 84: 2406–2410.

9. Hwang, L. S., Park, J., Gilboa, E. (1984). Role of intron-contained sequences in the formation of the Moloney murine leukemia virus env mRNA. Mol. Cell Biol. 4: 2289–2297.

10. Kadesh, T. and Berg, P. (1986). Effects of the position of the simian virus 40 enhancer on expression of multiple transcription units in a single plasmid. Mol. Cell Biol. 6: 2593–2601.

11. Kantoff, P. W., Kohn, D. B., Mitsuya, H., Armentano, D., Sieberg, M., Zwiebel, J. A., Eglitis, M. A., McLachlin, J. R., Wiginton, D. A., Hutton, J. J., Horowitz, D. A., Gilboa, E., Blaese, R. M. and Anderson, F. W., (1986). Correction of adenosine deaminase deficiency in human T and B cells using retroviral-mediated gene transfer. Proc. Natl. Acac. Sci. USA 83: 6563–6567.

12. Lobel, M.,. Patel, M., King, W., Nguyen-Huu, M. and Goff, S. (1985). Construction and recovery of viable retroviral genomes carrying a bacterial suppressor transfer rNA Gene. Science, 228: 329–332.

13. Miller, D. A. and Buttimore, C. (1986). Redesign of retrovirus packaging cell lines to avoid recombination leading to helper virus production. Mol. Cell. Biol. 6: 2895–2902.

14. Miller, A. D., Ong. E. S., Rosenfeld, M. G., Verma, I. M. and Evans, R. M. (1984). Infectious and selectable retrovirus containing an inducible rat growth hormone minigene. Science, 225: 993–998.

15. Miller, C. K. and Temin, H. M. (1986). Insertion of several different DNAs in retriculoendotheliosis virus strain T suppresses transformation by reducing the amount of subgenomic mRNA. J. Virol. 58: 75–80.

16. Reik, W., Weiher, H. and Jaenisch, R. (1985). Replication competent Moloney murine leukemia virus carrying a bacterial suppressor tRNA gene: Selective cloning of proviral and flanking host sequences. Proc. Natl. Acad. Sci. 82: 1141–1145.

17. Spencer, N., Hopkinson, D. A. and Harris, H. (1968). Adenosine deaminase polymorphism in man. Ann. Hum. Genet. 32: 9–14.

18. Temin, H. (1986). Retrovirus vectors for gene transfer: efficient integration into and expression of exogenous DNA in vertebrate cell genomes. In Gene Transfer (editor: R. Kucherlapati), Plenum Press, New York.

19. Varmus, H. and Swanstrom, L. (1985). Replication of retroviruses. (R. Weiss, N. Teich, H. Varmus and J. Coffin, eds.) RNA Tumor Viruses, Cold Spring Harbor Press, Cold Spring Harbor, N.Y., pages. 369–512.

20. Winginton, D. A., Kaplan, D. J., States, J. C., Akeso, A. L., Persune, C. N., Bilyk, I. J., Vaughn, A. J., Lattier, D. L. and Hutton, J. J. (1986). Complete sequence and structure of the gene for human adenosine deaminase. Biochemistry 25: 8234–8244.

21. Winginton, D. A., Adrian, G. S., Freidman, R. L., Suttle, D. P. and Hutton, J. J. (1983). Cloning of cDNA sequences of human adenosine deaminase. Proc. Natl. Acad. Sci. (USA) 80: 7481–7485.

22. Yee, J-K, Moores, J. C., Jolly, D. J., Wolff, J. A., Respess, J. G. and Friedmann, T. (1987). Gene expression from transcriptionally disabled retroviral vectors. Proc. Natl. Acad. Sci. 84: 5197–5201.

23. YU, S-F., yon Ruden, T., Kantoff, P. W., Garber, C., Seiberg, M., Ruther, U., Anderson, W. F., Wagner, E.F. and Gilboa, E. (1986). Self-inactivating retroviral vectors designed for transfer of whole genes into mammalian cells. Proc. Natl. Acad. Sci. USA 83: 3194–3198.

24. Chirgwin, J. M., Przybyla, A. E., MacDonald, R. J., and Rutter, W. J. (1979).Biochemistry, 18: 5294–5299.

25. Lehrach, M. Diamond, D., Wozney, J. W. and Boedtker (1977) Biochemistry 16: 4743–4751.

26. Fan, H., Mittal, S., Chute, H., Chao, E. and Pattengale, P. K. (1986) J. Vir. 60: 204–214.

27. Rhode, B. W., Emerman, M., Temin, H. M. (1987) J. Vir. 61: 925–927.

28. Proudfoot, N. J. (1986) Nature 322: 562–565.

29. McIvor, R. S., Johnson, J. M., Miller, D. A., Pitts, S., Williams, S. R., Valerio, D., Martin, D. W. Jr., and Verma, L M. (1987) Mol. Cell. Biol. 7: 838–846.

30. Bowtell, D. D. L., Cory, S., Johnson, G. R. and Thomas, G. J. (1988) J. Vir. 62: 2464–2473.

31. Kahn, P. M. (1971) Arch. Biochem. Biophys. 145: 470–483.

What is claimed is:

1. A retroviral vector comprising a 5' long terminal repeat (LTR), a 3' LTR, and a transcription unit inserted only into the U3' region of the 3' LTR, wherein the transcription unit comprises a promoter and a DNA sequence capable of being transcribed into RNA under control of the promoter, so that the DNA sequence is capable of being expressed in a eucaryotic cell infected with the retroviral vector, and wherein infection of the eucaryotic cell with the retroviral vector results in the transcription unit being duplicated and appearing in both the 5' and 3' LTR of the retroviral vector.

2. A retroviral vector of claim 1, comprising a proviral transcript of an entire retrovirus.

3. A retroviral vector of claim 1, comprising a proviral transcript of a portion of a retrovirus, said portion including both the 5' LTR and the 3' LTR of the retroviral vector.

4. The retroviral vector of claim 1, comprising a proviral transcript of an arian or of a murine retrovirus.

5. The retroviral vector of claim 4, wherein the arian retrovirus is an arian sarcoma virus, and the murine retrovirus is selected from the group consisting of a murine sarcoma virus and a murine leukemia virus.

6. The retroviral vector of claim 5, wherein the murine leukemia virus is mouse Moloney leukemia-virus (M-MuLV).

7. The retroviral vector of claim 1, comprising the retroviral vector N2.

8. The retroviral vector of claim 1, wherein the DNA sequence of the transcription unit is the human ADA mini gene.

9. The retroviral vector of claim 1, wherein the promoter of the transcription unit is selected from the group consisting of a pol I, a pol II, and a pol III promoter.

10. The retroviral vector of claim 1, wherein the DNA sequence encodes an antisense RNA molecule.

11. The retroviral vector of claim 1, wherein the DNA sequence encodes a recognition sequence for a nucleic acid binding protein.

12. The retroviral vector of claim 1, wherein the RNA is a mRNA molecule.

13. The retroviral vector of claim 1, wherein the DNA sequence expresses a selectable or identifiable phenotypic trait.

14. The retroviral vector of claim 13, wherein the selectable or identifiable phenotypic trait is resistance to neomycin.

15. The retroviral vector of claim 1, wherein the DNA sequence encodes a non-selectable trait.

16. The retroviral vector of claim 1, wherein the DNA sequence encodes a polypeptide.

17. The retroviral vector of claim 16, wherein the polypeptide is a mammalian polypeptide.

18. The retroviral vector of claim 17, wherein the mammalian polypeptide is a hemoglobin protein.

19. The retroviral vector of claim 1, wherein the transcription unit is inserted into the U3 region of the 3'LTR, upstream of the enhancer and promoter sequences of the 3'LTR.

20. The retroviral vector of claim 1, wherein the transcription unit is inserted into the U3 region of the 3' LTR, downstream of the enhancer sequence of the 3' LTR.

21. The retroviral vector of claim 1, wherein the transcription unit is inserted into the U3 region of the 3' LTR, downstream of the promoter sequence of the 3' LTR.

22. The retroviral vector of claim 1, wherein U3 region of the 3'LTR has the enhancer sequence deleted or modified so that the enhancer sequence is functionally inactive.

23. The retroviral vector of claim 1, wherein the U3 region of the 3'LTR has the promoter sequence deleted or modified so that the promoter sequence is functionally inactive.

24. The retroviral vector of claim 1, wherein the U3 region of the 3'LTR has the promoter and enhancer sequences deleted or modified so that the promoter and enhancer sequences are functionally inactive.

25. The retroviral vector of claim 1, further comprising a second, non-retroviral DNA sequence inserted between the 5'LTR and 3'LTR of the retroviral vector.

26. The retroviral vector of claim 25, wherein the second, non-retroviral DNA sequence expresses a selectable or identifiable phenotypic trait.

27. The retroviral vector of claim 26, wherein the selectable or identifiable phenotypic trait is resistance to neomycin.

28. The retroviral vector of claim 25, wherein the second, non-retroviral DNA sequence encodes a non-selectable trait.

29. The retroviral vector of claim 25, wherein the second, non-retroviral DNA sequence encodes both a selectable or identifiable phenotypic trait and a non-selectable trait.

30. A method of producing a virion comprising transfecting the retroviral vector of claim 1 into a retroviral packaging cell line and treating the transfected packaging cell line under conditions such that the virion is formed and produced therefrom.

31. A virion produced by the method of claim 30.

32. A method of introducing a transcription unit into a eucaryotic cell comprising infecting the cell with the virion of claim 31, wherein the transcription unit is incorporated into the chromosomal DNA of the eucaryotic cell.

33. The method of claim 32, wherein the eucaryotic cell is a mammalian cell.

34. The method of claim 33, wherein the mammalian cell is a hemopoietic stem cell.

* * * * *